United States Patent [19]

Larson et al.

[11] Patent Number: 4,939,140
[45] Date of Patent: Jul. 3, 1990

[54] HETEROCYCLIC OXOPHTHALAZINYL ACETIC ACIDS

[75] Inventors: Eric R. Larson, Guilford; Banavara L. Mylari, Waterford, both of Conn.

[73] Assignee: Pfizer Inc., New York, N.Y.

[21] Appl. No.: 263,577

[22] Filed: Oct. 27, 1988

Related U.S. Application Data

[63] Continuation-in-part of Ser. No. 136,179, Dec. 21, 1987, which is a continuation-in-part of Ser. No. 916,127, Oct. 7, 1986, abandoned, which is a continuation-in-part of Ser. No. 796,039, Jul. 11, 1985, abandoned.

[51] Int. Cl.$^5$ ............... C07D 237/32; C07D 519/00; A61K 31/50

[52] U.S. Cl. ..................................... 514/222; 514/225; 514/226; 514/228; 514/230; 514/231; 514/232; 514/234; 514/236; 514/241; 514/242; 514/243; 514/248; 544/3; 544/8; 544/11; 544/12; 544/49; 544/50; 544/51; 544/54; 544/58.6; 544/63; 544/66; 544/67; 544/73; 544/80; 544/96; 544/105

[58] Field of Search ............... 544/237, 3, 8, 11, 12, 544/49–51, 54, 58.6, 63, 66, 67, 73, 80, 96, 105, 112, 113, 116, 119, 182, 183, 215, 235; 514/222, 225, 226, 228, 230–232, 234, 236, 241–243, 248

[56] References Cited

U.S. PATENT DOCUMENTS 4,120,960 10/1978 Bristow .............................. 544/237

FOREIGN PATENT DOCUMENTS 222576 5/1977 European Pat. Off. .

OTHER PUBLICATIONS

Foldeak, Khim. Pharm. Zh., 1970, 4(5), 22–6, 1970—English Translation.
Mylari, Chem. Abs. 107, 176055p, (May 20, 1977).
Foldeak, Chem. Abs. 73, 77173y, (1970).

Primary Examiner—Mark L. Berch
Attorney, Agent, or Firm—Peter C. Richardson; Paul H. Ginsburg; Gezina Holtrust

[57] ABSTRACT

A heterocyclic oxophthalazinyl acetic acid having aldose reductast inhibitory activity of the formula

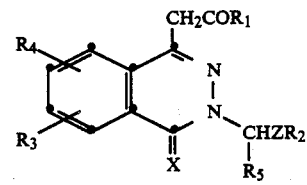

wherein X is oxygen or sulfur; Z is a covalent bond, O, S, NH or $CH_2$ or $CHR_5Z$ is vinyl; $R_1$ is hydroxy, or a prodrug group; $R_2$ is a heterocyclic group, $R_3$ and $R_4$ are hydrogen or the same or a different substituent, and $R_5$ is hydrogen, methyl or trifluoromethyl. The pharmaceutically acceptable acid addition salts of the above compounds wherein $R_1$ is di($C_1$–$C_4$)alkylamino or ($C_1$–$C_4$)alkoxy substituted by N-morpholino or di($C_1$–$C_4$)alkylamino and the pharmaceutically active base addition salts of the above compounds wherein $R_1$ is hydroxy are also aldose reductase inhibitors.

29 Claims, No Drawings

HETEROCYCLIC OXOPHTHALAZINYL ACETIC ACIDS

CROSS-REFERENCE

This is a continuation-in-part of 07/136,179 filed Dec. 21, 1987, which is a continuation in part of Ser. No. 916,127 filed Oct. 7, 1986, now abandoned, which is a continuation in part of application Ser. No. 796,039 filed July 11, 1985, now abandoned.

BACKGROUND OF THE INVENTION

This invention relates to novel heterocyclic oxophthalazinyl acetic acids useful in the treatment of certain chronic complications arising from diabetes mellitus, such as diabetic cataracts, retinopathy and neuropathy, to pharmaceutical compositions containing such compounds and to a method of using these compounds.

In the past various attempts have been made to obtain more effective oral anti-diabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Patent No. 3,821,383 discloses aldose reductase inhibitors like 1,3-dioxo-1H-benz[d,e]-isoquinoline-2-(3H)-acetic acid and derivatives thereof to be useful for the treatment of these conditions. U.S. Pat. No. 4,226,875 teaches the use of spiro-oxazolidinediones for treating complications of diabetes as aldose reductase inhibitors. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way unwanted accumulations of galactitol in the lens of galactosemic subjects and of sorbitol in the lens, peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

U.S. Pat. No. 4,251,528 discloses aromatic carbocyclic oxophthalazinyl acetic acids having aldose reductase inhibiting properties. The patent mentions that 2-(2-pyrid-2-ylethyl)-3,4-dihydro-4-oxophthalazin1-ylacetic acid does not inhibit aldose reductase.

SUMMARY OF THE INVENTION

According to the invention, compounds are provided having the formula

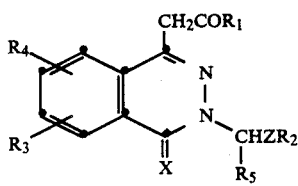

I wherein
X is oxygen or sulfur;
Z is a covalent bond, O, S, NH or $CH_2$, or $CHR_5Z$ is a vinylene group;
$R_1$ is hydroxy, or a prodrug group; $R_2$ is a heterocyclic 5-membered ring having one nitrogen, oxygen or sulfur, two nitrogens one of which may be replaced by oxygen or sulfur, or three nitrogens one of which may be replaced by oxygen or sulfur, said heterocyclic 5-membered ring substituted by one or two fluoro, chloro, $(C_1-C_4)$alkyl or phenyl, or condensed with benzo, or substituted by one of pyridyl, furyl or thienyl, said phenyl or benzo optionally substituted by one of iodo, cyano, nitro, perfluoroethyl, trifluoroacetyl, or $(C_1-C_4)$alkanoyl, one or two of fluoro, chloro, bromo, hydroxy, $(C_1-C_4)$alkyl, $(C_1-C_4)$alkoxy, $(C_1-C_4)$alkylthio, trifluoromethoxy, trifluoromethylthio, $(C_1-C_4)$alkylsulfinyl, $(C_1-C_4)$alkylsulfonyl or trifluoromethyl, or two fluoro or two trifluoromethyl with one hydroxy or one $(C_1-C_4)$alkoxy, or three fluoro, said pyridyl, furyl or thienyl optionally substituted in the 3-position by fluoro, chloro, bromo, $(C_1-C_4)$alkyl or $(C_1-C_4)$alkoxy; a heterocyclic 6-membered ring having one to three nitrogen atoms, or one or two nitrogen atoms and one oxygen or sulfur, said heterocyclic 6-membered ring substituted by one or two $(C_1-C_4)$alkyl or phenyl, or condensed with benzo, or substituted by one of pyridyl, furyl or thienyl, said phenyl or benzo optionally substituted by one of iodo or trifluoromethylthio, or one or two of fluoro, chloro, bromo, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, or trifluoromethyl, and said pyridyl, furyl or thienyl optionally substituted in the 3-position by fluoro, chloro, $(C_1-C_4)$alkyl or $(C_1-C_4)$alkoxy; said benzo-condensed heterocyclic 5-membered or 6-membered rings optionally substituted in the heterocyclic 5-membered or 6-membered ring by one of fluoro, chloro, bromo, methoxy, or trifluoromethyl; oxazole or thiazole condensed with a 6-membered aromatic group containing one or two nitrogen atoms, with thiophene or with furane, each optionally substituted by one of fluoro, chloro, bromo, trifluoromethyl, methylthio or methylsulfinyl; imidazolopyridine or triazolopyridine optionally substituted by one of trifluoromethyl, trifluoromethylthio, bromo, or $(C_1-C_4)$alkoxy, or two of fluoro or chloro; thienothiophene or thienofuran optionally substituted by one of fluoro, chloro or trifluoromethyl; thienotriazole optionally substituted by one of chloro or trifluoromethyl; naphthothiazole; naphthoxazole; or thienoisothiazole; with the proviso that $R_2$ is not pyridyl substituted by one or two $(C_1-C_4)$alkyl or phenyl; $R_3$ and $R_4$ are the same or different and are hydrogen, fluoro, chloro, bromo, trifluoromethyl, $(C_1-C_4)$alkyl, $(C_1-C_4)$alkoxy, $(C_1-C_4)$alkylthio, $(C_1-C_4)$alkylsulfonyl, or nitro, or $R_3$ and $R_4$ taken together are $(C_1-C_4)$alkanylenedioxy; and $R_5$ is hydrogen, methyl or trifluoromethyl; or a pharmaceutically acceptable base addition salt of a compound of formula I wherein $R_1$ is hydroxy, or an acid addition salt of a compound of formula I wherein prodrug group $R_1$ is di$(C_1-C_4)$alkylamino or $(C_1-C_4)$alkoxy substituted by N-morpholino or di$(C_1-C_4)$alkylamino.

More specific compounds of the invention are those wherein X is oxygen and those wherein $R_2$ is optionally substituted benzothiazolyl, benzoxazolyl, isoquinolyl, benzothiophen-yl, benzofuran-yl or benzimidazolyl, or substituted oxadiazolyl or indolyl. Other more specific compounds are those wherein $R_5$ is trifluoromethyl, X is oxygen, Z is a covalent bond or CH$_2$, R$_1$ is hydroxy, and R$_3$ and R$_4$ are hydrogen.

Preferred compounds of the invention are those wherein X is oxygen, Z is a covalent bond, R$_1$ is hydroxy, R$_2$ is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, benzothiophen-2-yl, benzofuran-2-yl, or thazolo[4,5-pyridine-2-y, thieno[2,3-b]pyridine2-yl, imidazo[1,5-a]pyridine-2-yl, or indol-2-yl, or substituted 1,2,4-oxadiazol-3-yl, 1,2,4-oxadiazol-5-yl, isothiazol-5-yl, isothiazol-4-yl, 1,3,4-oxadiazol-5-yl, 1,2,5-thiadiazol-3-yl, oxazol-2-yl, thiazol-2-yl, or thiazol-4-yl, and R$_3$, R$_4$ and R$_5$ are hydrogen.

Other preferred compound are those wherein the methylene bridge connecting the oxophthalazinyl group with R$_2$ is located alpha with respect to a nitrogen atom in R$_2$, e.g. wherein R$_2$ is benzoxazol-2-yl or 1,2,4-oxadiazol-3-yl mentioned above.

Other more specific compounds of the invention are those wherein X is oxygen, Z is a covalent bone, R$_1$ is hydroxy, R$_2$ is optionally 4,5,6 or 7 benzo-substituted benzothiazolyl, benzoxazolyl, benzimidazolyl, benzothiophenyl, benzofuranyl, or indolyl, or R$_2$ is 2-benzothiazolyl substituted in the benzo by one trifluoroacetyl or trifluoromethylthio, or one or two of fluoro chloro, bromo, hydroxy, methyl, methoxy, trifluoromethyl, trifluoromethoxy, trifluoromethylthio, or two fluoro or two trifluoromethyl with one methoxy, or three fluoro, or by 6,7-benzo, and those wherein R$_3$ is hydrogen, 5-fluoro, 5-chloro, 5-bromo or 5-methyl, and R$_4$ is hydrogen, 6- or 7- substituted chloro, bromo, methyl, isopropyl, methoxy, nitro or trifluoromethyl; or R$_3$ and R$_4$ is 4,5-difluoro; and those wherein R$_2$ is optionally substituted benzothiazol-2-yl or quinoxalyl and R$_3$ and R$_4$ are each chloro.

Further more specific compounds are those wherein X is oxygen, Z is a covalent bond, R$_1$ is hydroxy, R$_2$ is optionally substituted benzothiazol-2-yl, R$_3$ and R$_4$ are hydrogen, and R$_5$ is methyl; those wherein X is oxygen, Z is a covalent bond, R$_1$ is hydroxy, R$_3$, R$_4$ and R$_5$ are hydrogen, and R$_2$ is optionally 4,5,6 or 7 benzosubstituted benzothiazolyl-2-trifluoromethyl, benzoxazolyl-2-trifluoromethyl, benzimidazolyl-2-trifluoromethyl, benzofuran-2-trifluoromethyl, benzofuran-3-trifluoromethyl, benzothiophen-2-trifluoromethyl, benzothiophen-3-trifluoromethyl, indolyl-2-trifluoromethyl, or indolyl-3-trifluoromethyl; and those wherein X is oxygen, Z is CHhd 2, R$_1$ is hydroxy, R$_2$ is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, or thiazolo[4,5-b]pyridine-2-yl, or substituted 1,2,4- oxadiazol3-yl, 1,2,4-oxadiazol-5-yl, isothiazol-5-yl, isothiazol4-yl, 1,3,4-oxadiazol-5-yl, 1,2,5-thiadiazol-3-yl, oxazol-2-yl, thiazol-2-yl, or thiazol-4-yl, and R$_3$, R$_4$ and R$_5$ are hydrogen.

Specific preferred compounds of formula I are 3-(5-bromo-2-benzothiazolylmethyl)-4-oxo-3H-phthalazin-1-yl-acetic acid, 3-(5-fluoro-2-benzothiazolylmethyl)-4-oxo-3H-phthalazin-1-ylacetic acid, 3-(5-trifluoromethyl-2-benzothiazolylmethyl)-4-oxo-3H-phthalazin-1-ylacetic acid, 3-(5-chloro-2-benzothiazolylmethyl)-4-oxo-3H-phthalazin-1-ylacetic acid, 3-(4,5-difluoro-2-benzothiazolylmethyl)-4-oxo-3H-phthalazin-1-ylacetic acid, 3-(5,7-difluoro-2-benzothiazolylmethyl)-4-oxo3H-phthalazin-1-yl, 3-(5,7-dichloro-2-benzothiazolyl- methyl)-4-oxo-3H-phthalazin-1-ylacetic acid, 3-(4,7-dichloro-2-benzothiazolylmethyl)-4-oxo-3H-phthalazin-1-ylacetic acid, and 3-(5,7-bistrifluoromethyl-2-benzothiazolylmethyl-4-oxo-3H-phthalazin-1-ylacetic acid.

The present invention also relates to a composition for inhibition of aldose reductase activity comprising a compound of formula I in an amount effective in the inhibition of aldose reductase activity, in admixture with a pharmaceutically acceptable carrier. Specific and preferred compositions contain the specific and preferred compounds of formula I as described above.

The invention further comprises a method of treating a diabetic host such as an animal or a human for diabetes-associated complications which comprises administering to the host an effective amount of a compound of formula I. Specific and preferred methods comprise administering specific and preferred compound of formula I as described above.

The invention includes a process for preparing a compound of the formula I defined above by reacting a compound of the formula

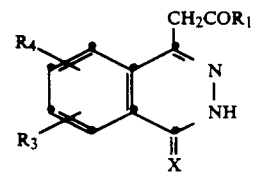

with a compound of the formula

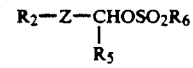

in an inert atmosphere, wherein R$_1$ is (C$_1$-C$_4$)alkoxy, X, Z, R$_2$, R$_3$, R$_4$ and R$_5$ are as defined in claim 1 and R$_6$ is (C$_1$-C$_4$)alkyl, trifluoromethyl, or phenyl optionally substituted by methyl, chloro, bromo or nitro.

DETAILED DESCRIPTION OF THE INVENTION

The numbering system of the compounds of formula I is as shown:

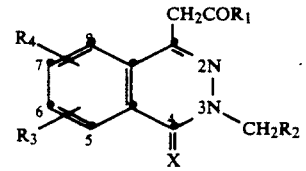

The term "(C$_1$-C$_4$)alkyl" whenever used in the definitions of R$_1$ to R$_4$ denotes saturated monovalent straight or branched aliphatic hydrocarbon radicals having one to four carbon atoms, such as methyl, ethyl, propyl, butyl, t-butyl etc.

The term "prodrug" denotes a group that is converted in vivo into the active compound of formula I wherein R$_1$ is hydroxy. Such groups are generally known in the art and include ester forming groups, to form an ester prodrug, such as benzyloxy, di(C$_1$-C$_4$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and (C$_1$-C$_4$)alkoxy optionally substituted by N-morpholino and amide-forming groups such as di(C$_1$-C$_4$)alkylamino.

The heterocyclic 5-membered ring having one to three nitrogenatoms, one of which may be replaced by oxygen or sulfur includes imidazolyl, oxazolyl, thiazolyl, pyrazolyl, oxadiazolyl, thiadiazolyl, and triazolyl.

The heterocyclic 6-membered ring having one to three nitrogen atoms, or one or two nitrogen atoms and one oxygen or sulfur includes triazinyl, pyrimidyl, pyridazinyl, oxazinyl and triazinyl.

The heterocyclic ring may be condensed with benzo so that said ring is attached at two neighboring carbon atoms to form a phenyl group. Such benzoheterocyclic ring may be attached to Z either through the heterocyclic group or through the benzo group of the benzoheterocyclic ring. The preparation of those compounds wherein Z is attached to the benzo group is illustrated in Reaction Scheme B below. Specific examples wherein said heterocyclic ring is condensed with a benzo include benzoxazolyl, quinazolin-2-yl, 2-benzimidazolyl, quinazolin-4-yl and benzothiazolyl. The oxazole or thiazole condensed with a 6-membered aromatic group containing one or two nitrogen atoms include positional isomers such as oxazolo[4,5-b]pyridine-2-yl, thiazolo[4,5-b]pyridine-2-yl, oxazolo[4,5-c]pyridine-2-yl, thiazolo[4,5-c]pyridine-2-yl, oxazolo[5,4-b]pyridine-2-yl, thiazolo[5,4-b]pyridine-2-yl, oxazolo[5,4-c]pyridine-2-yl, and thiazolo[5,4-c]pyridine-2-yl.

The compounds of the invention are prepared as outlined in Reaction Scheme A.

Phthalic anhydride and its derivatives of formula II are either commercially available or may be prepared according to standard procedures. The compounds of formula III wherein R' is ethyl or methyl may be prepared by reacting the compounds (II) with (carbethoxymethylene)triphenylphosphorane or (carbomethoxymethylene)triphenylphosphorane, respectively, in the Wittig reaction described in the prior art such as U.S. Pat. No. 4,251,528 and Tetrahedron Letters, 1965, 2357.

The compounds of formula IV wherein R' is methyl or ethyl may be formed by reacting compounds (III) with hydrazine as described in U.S. Pat. No. 4,251,528. Preferably, the reaction is carried out in an aqueous solvent such as aqueous ethanol, dioxane or dimethylformamide, and at 40° to 120° C., preferably, at reflux temperature.

The compounds of formula V are formed on reacting compounds (IV) wherein R' is hydrogen, methyl or ethyl, with

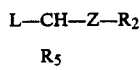

wherein L is a leaving group capable of forming compound LH on reaction of said two reagents. L is for example chloro, bromo, or $OSO_2R_6$, wherein $R_6$ is $(C_1-C_4)$alkyl, trifluoromethyl, phenyl or phenyl substituted by methyl, chloro, bromo or nitro.

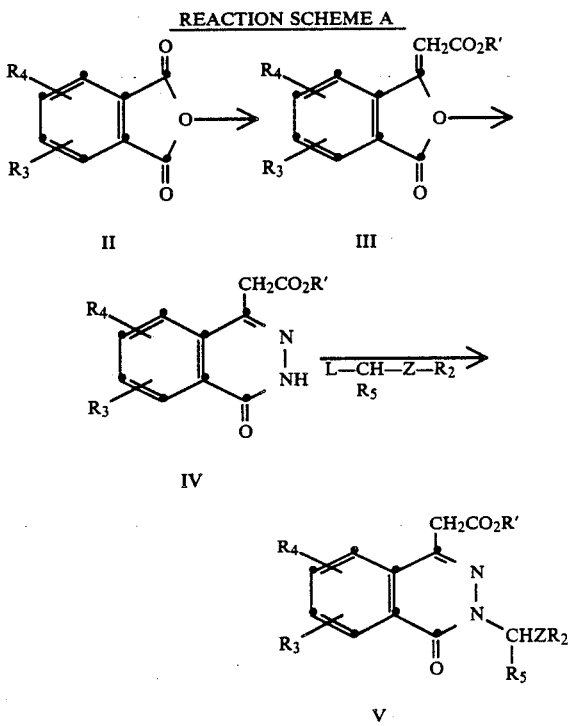

When reacting compounds (IV) wherein R' is methyl or ethyl, the process is generally carried out in a polar solvent such as an alkanol having 1 to 4 carbon atoms, e.g. methanol or ethanol, dioxan, dimethylformamide, or dimethylsulfoxide, in the presence of a base. Suitable bases are alkali metal hydride or alkoxide of 1 to 4 carbon atoms, such as sodium or potassium hydride, methoxide or ethoxide. When a hydride is used, a non-aqueous solvent such as dimethylformamide is required. When reacting compounds (IV) wherein R' is hydrogen, obtained on hydrolysis of compounds (IV) wherein R' is methyl or ethyl, it is necessary for at least two molar equivalents of the base to be present, since the first molar equivalent reacts with the carboxylic acid radical of such a compound. In addition, when reacting such compounds, it is preferable to use a hydroxylic solvent to minimize production of a corresponding ester.

The reaction to form compounds (V) wherein $R_5$ is methyl or trifluoromethyl is preferably performed with compounds of formula

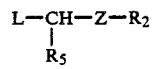

wherein $R_5$ is methyl or trifluoromethyl, and $OSO_2R_6$ wherein $R_6$ is as defined above. This reaction is generally conducted in an inert atmosphere such as nitrogen in an aprotic polar solvent such as dimethylformamide at temperatures of 20° to 50° C.

The reaction to form compound (V) may be at room temperature, or at higher temperatures to accelerate the process.

The compounds of formula V wherein R' is methyl or ethyl may be hydrolyzed to obtain compounds of formula I wherein $R_1$ is hydrogen. The hydrolysis proceeds at conventional temperatures and in the presence of acid or base such as a mineral acid, for example hydrochloric acid, or an alkali metal hydroxide or carbonate such as sodium or potassium hydroxide or carbonate. The reaction is carried out in the presence of water and a solvent, for example an alkanol of 1 to carbon atoms such as methanol, or dioxane.

The compounds of formula I wherein $R_1$ is hydroxyl may be esterified by conventional methods such as reaction of the corresponding acid chloride, bromide or anhydride with $R_1H$ to obtain compounds (I) wherein $R_1$ is an ester prodrug group. Alternatively, the compounds of formula I in which $R_1$ is an ester prodrug group may be prepared by alkylating a solution of the sodium salt of a compound (I) wherein $R_1$ is hydroxy. The alkylating agent may be a chloride. For instance, when $R_1$ is benzyloxy, acetoxymethyl, or pivaloyloxymethyl, then the alkylating agent is benzylchloride, chloromethylacetate or chloromethylpivalate, respectively. The above sodium salt is generally prepared in situ by reacting a compound (I) wherein $R_1$ is hydroxy with a sodium salt forming compound such as sodium bicarbonate, sodium hydride or sodium t-butylammonium sulfate in a non-aqueous solvent such as dimethylformamide or methylpyrrolidone.

When $R_1$ in compounds of formula (I) is an amide prodrug group such as $di(C_1-C_4)alkylamino$, a compound (I) wherein $R_1$ is $(C_1-C_4)alkoxy$ is converted to the corresponding amide by reaction with an amine, e.g. $di(C_1-C_4)alkylamine$.

The compounds of formula I wherein X is sulfur are prepared by thiating the corresponding compounds (I) wherein X is oxygen by known procedures, for example by reaction with phosphorus pentasulphide.

An alternative method for forming the benzothiazolyl-substituted compounds of formula I is described in copending application Ser. No. 059,899 filed on June 9, 1987 by the same inventors as the inventors of the present application. Thus, those compounds of formula I wherein $R_2$ is an optionally substituted benzothiazol-2-yl group may be prepared by reacting a compound of the formula

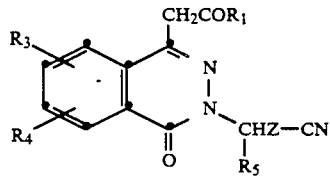

wherein $R_1$ is hydroxy or $C_1-C_4$ alkoxy, $R_3$, $R_4$ and $R_5$ are as defined above for the compounds of formula I, and Z is a covalent bond or $CH_2$, with an acid addition salt of optionally substituted 2-amino-thiophenol.

The compounds of formula

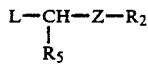

wherein L is chloro, Z is a covalent bond, $R_5$ is hydrogen, and $R_2$ is oxazole or thiazole condensed with Y wherein Y together with two adjacent carbons of the oxazole or thiazole forms a 6-membered aromatic group containing one or two nitrogen atoms, thiophene or furane, each optionally substituted by $R_8$ where $R_8$ is one of fluoro, chloro, bromo, trifluoromethyl, methylthio or methylsulfinyl; or Y is 1,2,4-oxadiazol-3-yl or 1,2,4-thiadiazol-3-yl optionally substituted by $R_7$ wherein $R_7$ is one of iodo or trifluoromethylthio, or one or two of fluoro, chloro, bromo, $(C_1-C_4)alkyl$, $(C_1-C_4)alkoxy$, $(C_1-C_4)alkylthio$, $(C_1-C_4)alkylsulfinyl$, $(C_1-C_4)alkylsulfonyl$ or trifluoromethyl, may be prepared by reacting compounds of the formula

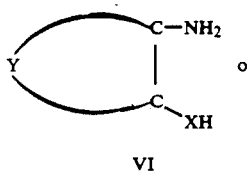 or 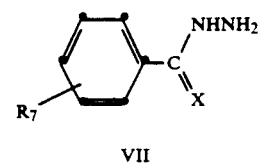

wherein X is 0 or S, and $R_7$ is as defined above, and Y together with the two carbons to which Y is attached is a 6-membered aromatic group containing one or two nitrogen atoms, thiophene or furane, each of said condensed Y- containing groups optionally substituted b $R_8$ as defined above, with $tri((C_1-C_4)alkoxy)CH_2Cl$. This reaction generally proceeds in a reaction-inert solvent such as a $(C_1-C_4)$ alcohol e.g. ethanol, halocarbons e.g. chloroform or methylene chloride, or ethereal solvents such as diglyme. The reaction temperature ranges from about room temperature to the reflux temperature of the solvent used. The reaction time may range from about 15 minutes to about 2 hours or more.

The starting materials (VI) and (VII) are either commercially available or may be prepared according to standard procedures, e.g. as described in J. Am. Chem. Soc. 53, 309(1935) and J. Org. Chem. 29, 2652(1964).

The $tri((C_1-C_4)alkoxy)CH_2Cl$ compounds are either known or may be prepared by reacting 1,1,1-trialkoxyethane with N-chlorosuccinimide, or with chlorine in pyridine and a chlorohydrocarbon solvent. The first chlorination reaction is generally carried out in a solvent, suitably a non-polar solvent such as carbontetrachloride or tetrachloroethylene. The reaction is conveniently carried out at temperatures ranging from about 40° C. to about the reflux temperature of the solvent. The reaction with chlorine in pyridine must be in the presence of a chlorohydrocarbon solvent having one or more chloro atoms and one to six carbon atoms, e.g. methylene chloride, chloroform or trichloroethane.

Reaction Scheme B exemplifies the preparation of 3-(benzothiazole-5-ylmethyl)-4-oxo-phthalazin-1-yl-acetic acid which is a compound according to the invention wherein $R_2$ is a benzo-heterocyclic ring with the benzo attached to the —$CHR_5Z$— bridge in the final compound. Other such compounds wherein $R_2$ is a benzo-heterocyclic ring with the benzo attached to the Z in the final compound may be made by a similar method. In Scheme B, 5-methylbenzothiazole is reacted with a brominating agent such as N-bromosuccinimide to form 5-bromomethylbenzothiazole which is then reacted with 4-oxo-3H-phthalazin-1-yl acetate to form ethyl 3-(5-methylbenzothiazolyl)-4-oxo-3H-phthalazin-1-yl acetate under conditions as outlined above with reference to Reaction Scheme A for the conversion of compounds (IV) to compounds (V).

REACTION SCHEME B

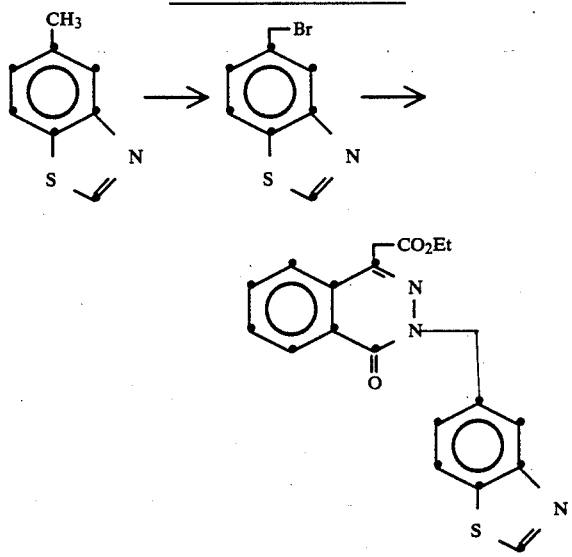

The pharmaceutically acceptable base addition salts of compounds (I) wherein $R_1$ is hydroxy may be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired metal and the solution subsequently evaporated to dryness. Suitable pharmaceutically acceptable cations for this purpose include, but are not limited to, alkali metal cations such as potassium and sodium, ammonium or water-soluble amine addition salts such as N-methylglucamine(meglumine), the lower alkanolammonium and other base salts with organic amines which are pharmaceutically acceptable, and alkaline earth metal cations such as calcium and magnesium. In general, the sodium and N-methylglucamine salts are preferred.

The pharmaceutically acceptable acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydroxhloric, hydrobromic, hydroiodic, sulfamic, sulfonic such as methanesulfonic, benzensulfonic, and related acids. Preferably, the acid is phosphoric acid.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention and alleviation of such conditions. The compound may be administered to a subject in need of treatment by a variety of conventional routes of administration, including orally, parenterally and topically. In general, these compounds will be administered orally or parenterally at dosages between about 0.5 and 25 mg./kg. body weight of the subject to be treated per day, preferably from about 1.0 to 10 mg./kg. However, some variation in dosage will necessarily occur depending on the condition of the subject being treated. The person responsible for administration will, in any event, determine the appropriate dose for the individual subject.

The novel compound of the invention may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitioneal administration. In this connection, the sterile aqueous media employed are all readily available by standard techniques known to those skilled in the art.

Compounds of formula I may not only be advantageously employed for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.). The ophthalmic preparation will contain a compound of formula I or a pharmaceutically acceptable salt thereof in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potassium borate, sodium and potassium carbonate, sodium acetate, sodium biphosphate and the like, in amounts sufficient to maintain the pH at between about 6 to 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e. diabetic, rats; (31) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; (5) measuring their ability to delay cataract formation and reduce the severity of lens opacities in chronic galactosemic rats; (6) measuring their ability to prevent sorbitol accumulation and cataract formation in isolated rat lens incubated with glucose; and (7) measuring their ability to reduce already elevated sorbitol levels in isolated rat lens incubated with glucose.

The present invention is illustrated by the following examples. It will be understood, however, that the invention is not limited to the specific details of these examples. Proton nuclear magnetic resonance spectra ('HNMR) were measured for solutions in deuterochoroform (CDCl₃) and peak positions are expressed in parts per million (ppm) downfield from tetramethylsilane (TMS). The peak shapes are denoted as follows: s, singlet; d, doublet; t, triplet; q, quartet; m, multiplet; br, broad.

EXAMPLE 1

3-(5-Bromobenzothiazol-2-yl-methyl)-4-oxo-3H-phthalazin-1-ylacetic acid (I; $R_1$=OH; $R_3$=$R_4$=H; $R_2$=5-bromobenzothiazol-2-yl; X=O)

A. 2,5-Dibromothioacetanilide

A mixture of 2,5-dibromoacetanilide (45.0 g), phophorous pentasulfide (24.4 g) and benzene (500 ml) was refluxed for 18 hours. After cooling the reaction mixture, the benzene layer was decanted off and then extracted with 10% potassium hydroxide solution (2×75 ml). The basic aqueous extract was washed with ether (2×50 ml), and acidified to pH 4.0 by the addition of diluted hydrochloric acid, and the precipitated 2,5-dibromothioacetanilide was collected and then air dried (Yield: 14.4 g; m.p. 119°–124° C.).

B. 2-Methyl-5-bromobenzothiazole

This compound was prepared by adapting the procedure described in Synthesis, 1976, 731. To a solution of 2,5-dibromothioacetanilide (9.27 g) in N-methyl-pyrrolidinone was cautiously added sodium hydride (1.93 g as 50% w/w dispersion in mineral oil). After the addition was complete, the mixture was heated at 150° C. for 1.5 hours. The dark reaction mixture was poured on to ice-water (300 ml.) and the separated brown gum was extracted with ethyl acetate (2×100 ml). The organic extract was washed with water (2×100 ml), dried over anhydrous magnesium sulfate and then evaporated. The resulting crude solid was chromatographed over silica gel to obtain the title compound (4.7 g; m.p. 84°–85° C.).

C. 2-Bromomethyl-5-bromobenzothiazole

A mixture of 2-methyl-5-bromobenzothiazole (32.0 g), N-bromosuccinimide (25.1 g), carbon tetrachloride (700 ml) and a catalytic amount of benzoyl peroxide (0.2 g) was refluxed under irradiation by an UV lamp for 14 hours. The reaction mixture was cooled to room temperature, filtered to remove the precipitated succinimide and the filtrate was evaporated to dryness. The resulting solid was chromatographed over silica gel to obtain the product (7.8 g; m.p. 107° C.).

D. Ethyl 3-(5-bromobenzothiazol-2-ylmethyl)-4-oxo-3H-phthalazin-1-ylacetate

To a mixture of ethyl 4-oxo-3H-phthalazin-1-ylacetate (11.6 g.) and sodium hydride (288 g; 50% w/w dispersion in mineral oil) in dimethylformamide (150 ml) was added 5-bromo-2-bromomethylbenzothiazole (16.8 g) and the resulting mixture stirred at room temperature for 1 hour. This reaction mixture was poured over ice-water (500 ml.); sufficient 10% HCl was added to adjust the pH to about 4.0 and the precipitated crude solid was collected. This was chromatographed over silica gel to obtain the product (yield: 5.6 g; m.p. 160°–161° C.).

E. 3-(5-Bromobenzothiazole-2-ylmethyl)-4-oxo-3H-phthalazin-1-ylacetic acid

A mixture of ethyl 3-(5-bromobenzothiazol-2yl- methyl)-4-oxo-3-H-phthalazin-1-ylacetate (15.0 g) and dioxane (150 ml) was brought to solution by warming on a steam bath and to this solution was added a solution of 10% potassium hydroxide (20 ml) in ethanol (50 ml.). The resulting dark purple solution was stirred at room temperature for 2 hours and concentrated to remove excess dioxane and ethanol. The concentrate was diluted with water (100 ml) and the resulting solution was washed with ether (2×100 ml). The aqueous layer was collected and acidified to pH 2.0 by addition of concentrated HCl. The precipitated solid was crystallized from methylene chloride/ethanol (400 ml/40 ml) to obtain the product (Yield 7.65 g; m.p. 214° C.).

EXAMPLE 2

3-(2-Pyridyl-1,2,4-oxadiazol-5-ylmethyl)-4-oxo-3H-phthalazin-1-ylacetic acid (I; $R_1$=OH; R $R_2$=2-pyridyl-1,2,4-oxadiazol-5-yl; X=O)

A. Pyridamidoxime

A mixture of 2-cyanopyridine (15 g), hydroxylamine hydrochloride (10 g), sodium carbonate (15.3 g) and ethanol (100 ml) was refluxed for 24 hours. The reaction mixture was cooled, filtered and the filtrate evaporated to obtain a solid, which was extracted with ethyl acetate. The organic extract was dried, evaporated and the residue crystallized from benzene (3.0 g; m.p. 113°–114° C.).

B. 3-(2-Pyridyl)-5-chloromethyl-1,2-4-oxadiazole

A mixture of pyridamidoxime (4.5 g), chloracetic anhydride (8.4 g) and toluene (350 ml) was refluxed for 12 hours. The hot solution was cooled, washed with water (2×100 ml), saturated bicarbonate solution (2×50 ml), again with water (2×100 ml) and the organic layer was evaporated to obtain a crude solid. This solid was crystallized from hexane to yield the product (3.4 g; m.p. 89°–94° C.).

C. Ethyl 3-(2-pyridyl-1,2,4-oxadiazol-5-ylmethyl)-4-oxo-3H-phthalazin-1-ylacetate To a solution of ethyl 4-oxo-3H-phthalazin-1-ylacetate (1.6 g) and sodium hydride (0.5 g; 50% w/w dispersion in mineral oil) in dimethylformamide (15 ml) was added 3-(2-pyridyl)-5-chloromethyl-1,2,4-oxadiazole (1.5 g) dropwise over a period of 40 minutes. After stirring for another 10 minutes, the reaction mixture was poured onto water (50 ml) and extracted with ether. The ether layer was evaporated and the residue was chromatographed over silica gel to obtain the product (1.0 g; m.p. 118°–128° C.).

D. 3-(2-Pyridyl-1,2,4-oxadiazol-5-ylmethyl)-4-oxo-3H-phthalazin-1-ylacetic acid To a solution of ethyl 3(2-pyridyl-1,2,4-oxadiazol5-ylmethyl)-4-oxo-3H-phthalazin-1-ylacetate (1.0 g) in methanol (10 ml) was added 20% aqueous KOH (0.5 ml) and the mixture refluxed for 30 minutes. Evaporation of excess methanol gave an orange residue. The residue was dissolved in water, acidified with acetic acid (1 ml) and the precipitated solid was collected and crystallized from isopropanol to yield the product (0.53 g; m.p. 196°–200° C.).

EXAMPLE 3

3-[3-(2-Trifluoromethylphenyl)-1,2,4-oxadiazol-5-ylmethyl]-4-oxo-3H-phthalazin-1-ylacetic acid (I; $R_1$=OH;
$R_3$=$R_4$=H;
$R_2$=3-(2-trifluoromethylphenyl)-1,2,4-oxadiazol-5-yl)

A. 3-[2-Trifluoromethylphenyl]-5-chloromethyl-2,3,4-oxadiazole

2-Trifluoromethylbenzimidioxime prepared similary to the procedure described in Ber, 1899, 32, (1975) (2.9 g; m.p. 115°–116° C.) starting from 2-trifluouromethylbenzaldehyde, was dissolved in anhydrous acetone (70 ml) and then solid potassium carbonate (2.0 g) was added. To the resulting slurry cooled to 15°–18° C. in an ice-water bath was added a solution of chloroacetyl chloride (1.1 ml) dissolved in acetone (10 ml). After the addition, the ice-bath was removed and the reaction mixture brought to room temperature and stirred for 1.5 hours. Evaporation of acetone gave a white residue which upon trituration with water yielded 0-chloroacetyl-2-trifluoromethylbenzimidoxine (3.0 g; m.p. 108°–110° C.). This product was mixed with tolune (50 ml) and heated to reflux for 1.5 hours. The toluene solution was cooled, washed with saturated aqueous sodium bicarbonate (10 ml) and water, and the organic portion was dried and evaporated. The resulting brown oil was chromatographed over silica gel to obtain the title compound as a yellow oil. 'HNMR(CDCl₃, 60MHz): 4.0 (s, 2H), 4.4 (s, 2H), 7.3 (s, 5H).

B. Ethyl 3-[3-(2-trifluoromethylphenyl)-1,2,4-oxadiazol-5-ylmethyl]-4-oxo-3H-phthalazin-1-ylacetate To a mixture of 4-oxo-3H-phthalazin-1-ylacetate (1.4 g) and sodium hydride (0.43 g; 50% w/w dispersion in mineral oil) in dimethylformamide (10 ml) was added 3-(2-trifluoromethylphenyl)-5-chloromethyl-1,2,4-oxadiazole (1.7 g) and the mixture was stirred at room temperature for 30 minutes. The reaction mixture was poured onto water (20 ml), acidified to pH 2.0 with 10% HCl and the precipitated solid collected. The solid was triturated with isopropanol to obtain the product as a white crystalline solid (1.65 g; m.p. 111°–115° C.).

C. 3-[3-(2-Trifluoromethylphenyl)-1,2,4-oxadiazol-5-ylmethyl]-4-oxo-3H-phthalazin-1-ylacetic acid A mixture of ethyl-3-[2-trifluoromethylphenyl)-1,2,4-oxadiazol-2-yl-methyl-4-oxo-phthalazin-1-ylacetate (1.6 g) and methanol (50 ml) containing 20 w/w aqueous KOH (0.5 ml) was heated on a steambath for 1 hour. Water (20 ml) was added to the residue obtained upon evaporation of methanol and the pH of the solution brought to 2 by addition of 10% HCl. The precipitated solid was crystallized from benzene (0.7 g; m.p. 132°–134° C.).

EXAMPLE 4

3-(N-methylbenzimidazol-2-ylmethyl)-4-oxo-3H-phthalazin-1-ylacetic acid (I; $R_1$=OH; $R_3$=$R_4$=H; X=O; $R_2$=3-(N-methylbenzimidazol-2-yl))

A. Ethyl 3-(N-methylbenzimidazol-2-ylmethyl)-4-oxo-3H-phthalazin-1-ylacetate)

A mixture of ethyl 4-oxo-3H-phthalazin-1-ylacetate (2.34 g) and sodium hydride (0.58 g; 50% w/w dispersion in mineral oil) in dimethylformamide (20 ml) was stirred at room temperature for 15 minutes. To this was added N-methyl-2-chlolomethylbenzimidazole (2.4 g; prepared according to JACS, 1943, 65 (1854) and stirred for another hour. It was poured onto water (150 ml) and extracted with ethyl acetate (2×100 ml). The organic extract was dried, evaporated and the residue was chromatographed over silica gel to obtain the product (2.04 g; m.p. 118° C.).

B. 3-(N-methylbenzimidazol-2-ylmethyl)-4-oxo-3H-phthalazin-1-ylacetic acid

To a solution of 3-(N-methylbenzimidazol-2-yl)-4-oxo-3H-phthalazin-1-ylacetate (2.0 g) in warm methanol (100 ml) was added 10% KOH (10 ml), stirred at room temperature for 2.5 hours and then evaporated to obtain a solid. This solid was dissolved in water (50 ml), extracted with ether (50 ml) and the aqueous layer was adjusted to pH 6.0 by the addition of acetic acid. The resulting white solid was collected, dried and crystallized from a mixture of methanol/methylene chloride to obtain the title compound (0.68 g; m.p. 230° C. (d)).

EXAMPLE 5

3-(Oxazolo[4,5-b]pyridine 2-ylmethyl)-4-oxo-3H-phthalazin-1-ylacetic acid (I; X=O; $R_1$=OH; $R_3$=$R_4$=H; $R_2$=oxazolo[4,5-b]pyridine-2-yl)

A solution obtained by adding ethyl 4-oxo-3H-phthalazin-1-ylacetate (1.25 g) to a suspension of sodium hydride (285 mg; 50% w/w dispersion in mineral oil) in dimethylformamide (10 ml) was added dropwise to a solution of 2-chloromethyl-oxazolo[4,5-b]pyridine (1.0 g) in dimethylformamide (5 ml). After 2 hours, the reaction mixture was poured onto cold water (20 ml) and extracted with ether. The ether extract was washed with water (2×50 ml), dried and evaporated. The resulting crude material was chromatographed over silica gel to obtain 3-(oxazolo[4,5-b]pyridine-2-ylmethyl)-4-oxo-3H-phthalazin-1-ylacetate (m.p. 105°-107° C.) which was used directly in the next step. The product was dissolved in methanol (5 ml) containing 20% aqueous potassium hydroxide (0.5 ml) and heated on a steam-bath for 15 minutes. The solution was evaporated to dryness, the residue dissolved in water and acidified with acetic acid (2 ml). The resulting yellow precipitate was collected, triturated with hot methanol and filtered to obtain the title compound as a white solid (0.32 g; m.p. 228°-230° C.).

EXAMPLE 6

A solution of methyl 3-(2-benzothiazolyl)-4-oxo-3H-phthalazin-1-ylacetate (1.92 g) in methanol (50 ml) containing 10% aqueous potassium hydroxide (5 ml) was stirred at room temperature for 4 hours. The solution was concentrated to remove methanol and the concentrate was diluted with water (75 ml) and then extracted with ethyl acetate. The aqueous portion was separated and acidified with concentrated hydrochloric acid to pH 2.0. The precipitated solid was collected and crystallized from isopropyl alcohol to give 3-(2-benzothiazolyl)-4-oxo-3-H-phthalazin-1-ylacetic acid (876 mg; m.p. 205° C.(d)).

EXAMPLE 7

In accordance with Example 6, the following compounds are prepared:

TABLE 1A

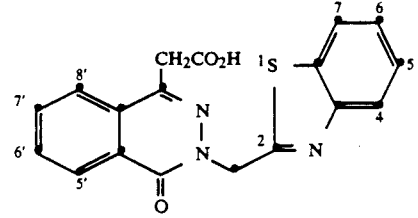

| Substituent | M.P. °C. |
| --- | --- |
| H | 205(d) |
| 4-Cl | 217(d) |
| 5-Cl | 210–212 |
| 6-Cl | 207(d) |
| 5-Br | 214 |
| 6-Br | 214 |
| 7-Br | 173–175 |
| 5-SCH₃ | 187–188 |
| 5-SOCH₃ | 184(d) |
| 5-SO₂CH₃ | 210–211(d) |
| 4-Cl, 5-Cl | 222 |
| 5-Cl, 6-Cl | 192–195 |
| 4-Cl, 6-Cl | 188–190 |
| 4-Cl, 7-Cl | 223–224 |
| 5-Cl, 7-Cl | 213 |
| 5-CH₃ | 205(d) |
| 6-CH₃ | 202(d) |
| 6-OCH₃ | 189(d) |
| 5′-F | 204–205 |
| 5′-CH₃ | 201–203 |
| 6,7-Benzo, 5′-F | 218–222 |
| 6,7-Benzo, 5′-CH₃ | 215–219 |
| 6′-Cl | 198–199 |
| 7′-Cl | 199 |
| 6′-Cl, 7′-Cl | 189–192 |
| 6-Br, 6′-Cl, 7′Cl | 206(d) |
| 6′-Br | 211 |
| 6′-CF₃ | 210–211 |
| 6′-NO₂ | 199–201 |
| 6′-OCH₃ | 177–179 |
| 4-OCH₃ | 200–201 |
| 5-OCH₃ | 195 |
| 4-OH | 165–166 |
| 5-OH | 154–156 |
| 5-OH, 7-OH | 184 |
| 4-CF₃ | 198 |
| 6-CF₃ | 194–195 |
| 5-CF₃, 7-CF₃ | 191–193 |
| 7′-Br | 192 |
| 7′-CH₃ | 187–190 |
| 7′-OCH₃ | 198–202 |
| 7′-CF₃ | 124–126 |
| 7′-NO₂ | 155–158 |
| 6,7-Benzo, 7′-Cl | 209–210 |
| 5-CF₃ | 197–198 |
| 6′-isopropyl | 184–185 |
| 7′-isopropyl | 99–101 |
| 4-F | 217–218 |
| 4-F, 5-F | 178–181 |
| 5-F, 7-F | 178 |
| 5-F | 222(d) |
| 6-isopropyl | 160–161 |

TABLE 1B

[Structure: phthalazinone with CH2CO2H group, linked via N-N-CH(R5)-Z to benzothiazole ring numbered 1S,2,4,5]

| Z | R5 | Substituent | M.P. °C. |
|---|---|---|---|
| covalent bond | CH3 | — | 159–160(d) |
| covalent bond | CH3 | 5-CF3 | 182–183 |
| covalent bond | CH3 | 5-Cl | 205 |
| sulphur | H | — | 150–160 |
| sulphur | H | 5-Cl | 100–104 |
| CH2 | H | 5-CF3 | 185 |

EXAMPLE 8

A mixture of methyl 4-oxo-3H-phthazalin-1-ylacetate (1.09 g) and sodium hydride (0.269 g; 50% w/w . dispersion in mineral oil) in dimethylformamide (25 ml) was stirred at room temperature for two hours under nitrogen. To the solution obtained was added 2-bromomethylbenzothiazole (1.14 g) dissolved in dimethylformamide (5 ml), the reaction mixture was stirred for an additional one hour and then poured into ice water (50 ml). The pH of the mixture was brought to 4.0 by addition of 10% hydrochloric acid (5 ml) and extracted with ethyl acetate (100 ml). The extract was washed with water (50 ml), dried (MgSO4) and evaporated. The crude product (1.92 g), methyl (2-benzothiazolyl)-4-oxo-3H-phthalazin-1-ylacetate, was characterized by NMR spectrum (see Table 2). The other compounds of Table 2 were prepared in a similar manner using the appropriate 4-oxo-3H-phthalazin-1-ylacetate and 2-bromomethylbenzothiazoles. The melting points are in degrees Centigrade.

TABLE 2A

[Structure: phthalazinone with CH2CO2R group, positions 5',6',7',8' on phthalazine ring, linked via N-N-CH2- to benzothiazole ring with positions 4,5,6,7]

| Substituent | R | Product |
|---|---|---|
| H | CH3 | 'HNMR(CDCl3, 60MHz) 3.6(s, 3H) 4.0(s, 2H), 5.7(s, 2H), 7.2(m, 2H), 7.6(m, 5H), 8.4(m, 1H) |
| 4-F | C2H5 | m.p. 119–120 |
| 5-F | C2H5 | m.p. 118–120 |
| 4-Cl | C2H5 | m.p. 113–116 |
| 5-Cl | C2H5 | m.p. 152–155 |
| 5-Br | CH3 | m.p. 160–161 |
| 7-Br | C2H5 | 'HNMR(CDCl3, 60MHz): 1.2 (t, J=8Hz, 3H), 4.1(s, 2H), 4.2 (q, J=8Hz, 2H), 5.8(s, 2H), 7.3 (m, 2H), 7.8(m, 4H), 8.4(m, 1H) |
| 5-CH3 | C2H5 | m.p. 134–136 |
| 4-F, 5-F | C2H5 | m.p. 118–122 |
| 5-F, 7-F | C2H5 | m.p. 115–117 |
| 4-Cl, 5-Cl | C2H5 | m.p. 121–122 |
| 5-Cl, 6-Cl | CH3 | 'HNMR(CDCl3, 90MHz): 3.70 (s, 3H), 4.00(s, 2H), 5.75(s, 2H), 7.6–8.0(m, 5H), 8.3–8.6(m, 1H) |
| 5-Cl, 7-Cl | C2H5 | m.p. 144–145 |
| 4-Cl, 6-Cl | CH3 | 'HNMR(CDCl3, 90MHz): 1.20(t, J= 8Hz, 3H), 4.00(s, 2H), 4.15(q, J=8Hz, 2H), 5.80(s, 2H) 7.40 (d, J=1Hz, 1H), 7.60(d, J=1Hz, 1H), 7.6–7.9(m, 3H), 8.4–8.6(m, 1H) |
| 4-Cl, 7-Cl | C2H5 | m.p. 173 |
| 6-OCH3 | CH3 | 'HNMR(CDCl3, 90MHz): 3.70 (s, 3H), 3.80(s, 3H), 4.05(s, 2H), 5.75(s, 2H), 7.00(dd, J=3, 9Hz, 1H) 7.20(d, J=3Hz, 1H), 7.6–7.9, (m, 4H), 8.4–8.6(m, 1H) |
| 5-CH3 | C2H5 | m.p. 123–124 |
| 6-CH3 | CH3 | 'HNMR(CDCl3, 90MHz): 2.50 (s, 3H), 3.75(s, 3H), 4.10(s, 2H), 5.90(s, 2H), 7.35(d, J=8Hz, 1H), 7.65–8.10(m, 4H), 8.5–8.7(m, 1H) |
| 6-isopropyl | C2H5 | H'NMR(CDCl3, 90MHz): 8.40 (m, 1H), 7.9–7.5(m, 5H), 7.2(d, J=9Hz, 1H), 5.79(s, 2H), 4.15(q, J=9Hz, 2H), 3.85(s, 2H), 2.98(Sep., J=9Hz, 1H), 1.28(d, J=9Hz, 6H), 1.20(5, J=9Hz, 3H) |
| 5'-F | C2H5 | 'HNMR(CDCl3, 90MHz): 1.20(t, J=8Hz, 3H), 4.00(s, 2H), 4.20(q, J=8Hz, 2H), 5.80(s, 2H), 7.2–8.1 (m, 7H) |
| 5'-CH3 | C2H5 | 'HNMR(CDCl3, 90MHz): 1.20(t, J=8Hz, 3H), 2.95(s, 3H), 3.95 (s, 2H), 4.20(q, J=8Hz, 2H), 5.75(s, 2H), 7.2–8.1(m, 7H) |
| 6,7-Benzo, 5'-F | C2H5 | 'HNMR(CDCl3, 90MHz): 1.20(t, J=8Hz, 3H), 3.95(s, 2H), 4.20(q, J=8Hz, 2H), 5.90(s, 2H), 7.25–8.00(m, 8H), 8.80(dd, J=3, 7Hz, 1H) |
| 6,7-Benzo, 5'-CH3 | C2H5 | 'HNMR(CDCl3, 90MHz): 1.20(t, J=8Hz, 3H), 2.95(s, 3H), 3.95 (s, 2H), 4.15(q, J=8Hz, 2H), 5.90 (s, 2H), 7.4–7.95(m, 8H), 8.80 (m, 1H) |
| 6'-Cl | C2H5 | 'HNMR(CDCl3, 90MHz): 1.20(t, J=8Hz, 3H), 4.05(s, 2H), 4.25 (q, J=8Hz, 2H), 5.85(s, 2H), 7.2–8.1(m, 6H), 8.50(d, J=2Hz, 1H) |
| 7'-Cl | C2H5 | 'HNMR(CDCl3, 90MHz): 1.25(t, J=8Hz, 3H), 4.00(s, 2H), 4.20 (q, J=8Hz, 2H), 5.80(s, 2H), 7.25–7.6(m, 2H), 7.65–7.90 (m, 3H), 8.00(dd, J=2, 9Hz, 1H), 8.45(d, J=9Hz, 1H) |
| 6'-Cl, 7'Cl | C2H5 | 'HNMR(CDCl3, 90MHz): 1.20(t, J=8Hz, 3H), 4.00(s, 2H), 4.20(q, J=8Hz, 2H), 5.80(s, 2H), 7.2–7.6 (m, 2H), 7.7–8.1(m, 3H), 8.55 (s, 1H) |
| 6'-Br | C2H5 | 'HNMR(CDCl3, 90MHz): 1.20(t, J=8Hz, 3H), 3.90(s, 2H), 4.15(q, J=8Hz, 2H), 5.80(s, 2H), 7.2–8.1 (m, 6H), 8.60(d, J=2Hz, 1H) |
| 6'-NO2 | C2H5 | 'HNMR(CDCl3, 90MHz): 1.20(t, J=8Hz, 3H), 4.05(s, 2H), 4.20(q, J=8Hz, 2H), 5.80(s, 2H), 7.2–7.6 (m, 2H), 7.7–8.1(m, 3H), 8.60(dd, J=2, 9Hz, 1H), 9.30(d, J=3Hz, 1H) |
| 6'-isopropyl | C2H5 | 'HNMR(CDCl3, 90MHz): 8.25(s, 1H), 7.9(m, 1H), 7.7(m, 3H), 7.3 (m, 2H), 5.8(s, 2H), 4.20(q, J=9Hz, 2H), 3.95(2, 2H), 3.1(sep., J=9Hz, 1H), 1.35(d, J=9Hz, 6H), 1.20(s, |

TABLE 2A-continued

[Structure diagram: phthalazine derivative with CH2CO2R group and benzothiazole ring with positions 4,5,6,7 labeled, and positions 5',6',7',8' on the phthalazine benzene ring]

| Substituent | R | Product |
|---|---|---|
| | | J=9Hz, 3H) |
| 6'-OCH$_3$ | C$_2$H$_5$ | 'HNMR(CDCl$_3$, 90MHz): 1.20(t, J=8Hz, 3H), 3.95(brs, 6H), 4.15(q, J=8Hz, 2H), 5.80(s, 2H), 7.20–8.10 (m, 7H) |
| 6'-CF$_3$ | C$_2$H$_5$ | 'HNMR(90MHz, CDCl$_3$): 8.7(s, 1H), 8.15–7.7(m, 4H), 7.40(m, 2H), 5.8 (s, 2H), 4.21(q, J=9Hz, 2H), 4.0 (s, 2H), 1.22(5, J=9Hz, 3H) |
| 7'Br | C$_2$H$_5$ | 'HNMR(CDCl$_3$, 90MHz): 1.20(t, J=8Hz, 3H), 3.90(s, 2H), 4.15(q, J=8Hz, 2H), 5.85(s, 2H), 7.15–7.50 (m, 2H), 7.6–8.1(m, 4H), 8.30 (d, J=9Hz) |
| 7'-CH$_3$ | C$_2$H$_5$ | 'HNMR(CDCl$_3$, 90MHz): 1.20(t, J=8Hz, 3H), 2.60(s, 3H), 4.15 (s, 2H), 4.20(q, J=8Hz, 2H), 5.80 (s, 2H), 7.3–8.2(m, 6H), 8.30(d, J=9Hz, 1H) |
| 7'isopropyl | C$_2$H$_5$ | 'HNMR(300MHz, CDCl$_3$): 8.24 (d, J=9Hz, 1H), 7.84(d, J=9Hz, 1H), 7.62(d, J=9Hz, 1H), 7.49 (d, J=9Hz, 1H), 7.36(s, 1H), 7.26("t", J=6Hz, 1H), 7.16 ("t", J=6Hz, 1H), 5.64(s, 2H), 4.06(q, J=9Hz, 1H), 1.30(d, J=9Hz, 6H), 1.17(t, J=9Hz, 3H) |
| 7'OCH$_3$ | C$_2$H$_5$ | 'HNMR(CDCl$_3$, 90MHz): 1.20(t, J=8Hz, 3H), 3.85(s, 3H), 3.90 (s, 2H), 4.20(q, J=8Hz, 2H), 5.80(s, 2H), 7.00(d, J=2Hz, 1H) 7.2–7.5(m, 3H), 7.75(dd, J=2.8Hz, 1H), 8.00(dd, J=2.7Hz, 1H), 8.50 (d, J=9Hz, 1H) |
| 7'CF$_3$ | C$_2$H$_5$ | 'HNMR(90MHz, CDCl$_3$): 8.90(d, J=9Hz, 1H), 8.15–7.70(m, 4H), 7.45–7.2(m, 2H), 5.8(s, 2H), 4.20(q, J=9Hz, 2H), 4.05(s, 2H), 1.18(t, J=9Hz, 3H) |
| 7'-NO$_2$ | C$_2$H$_5$ | 'HNMR(CDCl$_3$, 90MHz): 1.20(t, J=8Hz, 3H), 4.05(s, 2H), 4.20 (q, J=8Hz, 3H), 5.80(s, 2H), 7.2–7.6(m, 3H), 7.6–8.1(m, 2H), 8.4–8.7(m, 2H) |
| 6,7-Benzo, 7'-Cl | C$_2$H$_5$ | 'HNMR(CDCl$_3$, 90MHz): 1.20(t, J=8Hz, 3H), 4.00(s, 2H), 4.20(q, J=8Hz, 2H), 5.90(s, 2H), 7.5–8.0(m, 7H), 8.45(d, J=9Hz, 1H), 8.75–8.90(m, 1H) |
| 5-CF$_3$ | C$_2$H$_5$ | m.p. 134–136° C. |
| 4-OCH$_3$ | C$_2$H$_5$ | m.p. 149–153° C. |
| 5-OCH$_3$ | C$_2$H$_5$ | m.p. 127–129° C. |
| 5-OCH$_3$, 7-OCH$_3$ | C$_2$H$_5$ | m.p. 154–155° C. |
| 4-CF$_3$ | C$_2$H$_5$ | m.p. 136–138° C. |
| 6-CF$_3$ | C$_2$H$_5$ | m.p. 138–139° C. |

TABLE 2B

[Structure diagram: phthalazine derivative with CH2CO2C2H5 group, CH—Z linker with R5 substituent, and benzothiazole ring]

| Z | R$_5$ | Substituent | Product |
|---|---|---|---|
| covalent bond | CH$_3$ | — | m.p. 117–118° C. |
| covalent bond | CH$_3$ | 5-CF$_3$ | m.p. 105–106° C. |
| covalent bond | CH$_3$ | 5-Cl | m.p. 86–88° C. |
| S | H | — | 'HNMR(CDCl$_3$, 60MHz): 1.2(t, J=9Hz, 3H), 3.85 (s, 2H), 4.2(9, J=9Hz, 2H), 6.0(s, 2H), 7.1–8.0(m, 7H), 8.2–8.4 (m, 1H) |
| CH$_2$ | H | 5-CF$_3$ | m.p. 111–114° C. |

EXAMPLE 9

To a mixture of ethyl-4-oxo-3H-phthalazin-1-ylacetate (23.4 g) in dimethylformamide (175 ml) maintained at 10° C. was added potassium t-butoxide (11.2 g) portion-wise over 5 minutes. The resulting orange-colored solution was brought to room temperature and 5-trifluoromethyl-2-chloromethylbenzothiazole in dimethylformamide (25 ml) was gradually added over 15 minutes. After stirring for an additional 30 minutes, the mixture was poured onto ice water (1500 ml). The precipitated solid was collected and washed with a mixture of isopropyl ether/n-hexane (250 ml/500 ml). The resulting light yellow solid, ethyl-3-(5-trifluoromethyl-2-benzothiazolylmethyl)-4-oxo-phthalazinlylacetate, was air dried (44.3 g), m.p. 134°–136° C.

EXAMPLE 10

According to the method of Example 1D, the following compounds were prepared:

[Structure diagram: phthalazine derivative with CH2CO2C2H5 group linked via N—N—CH2 to a benzoxazole ring with positions 4,5,6,7]

| Benzoxazolyl substituent | Product |
|---|---|
| H | not isolated |
| 5-Cl | not isolated |
| 5-Br | not isolated |
| 5-CF$_3$ | m.p. 105–108° C. |
| 5-Cl, 7-Cl | Mass Spectrum, m/e base peak 431.06 (partly isolated) |
| 5,6-benzo | m.p. 167–170° C. |
| 5-F, 7-F | m.p. 68–69° C. |

According to the method of Example 6, the following compounds were prepared from the above compounds without isolation thereof.

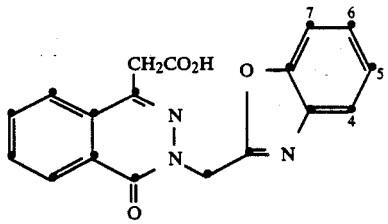

| Benzoxazolyl substituent | M.P. °C. |
|---|---|
| H | 179–183 |
| 5-Cl | 205–207 |
| 5-Br | 190–192 |
| 5-CF$_3$ | 196–198 |
| 5-Cl, 7-Cl | 199–201 |
| 5,6-benzo | 167–170 |
| 5-F, 7-F | 68–69 |

EXAMPLE 11

In accordance with Example 3B, the following compounds were prepared.

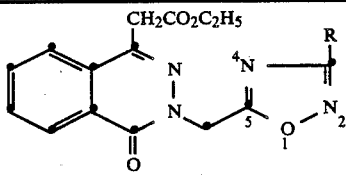

| R | Product |
|---|---|
| 2-F, 6-Cl-phenyl | 'HNMR(CDCl$_3$, 60MHz): 1.3(t, J=8Hz, 3H), 4.0 (s, 2H), 4.2(q, J=8Hz, 2H) 5.8(s, 2H), 7.3(m, 3H), 7.8(m, 3H), 8.4(m, 1H) |
| 2-pyridyl | m.p. 118–123° C. |
| 2-Br-phenyl | 'HNMR(CDCl$_3$, 60MHz): 1.3(t, J=8Hz, 3H), 4.0 (s, 2H), 4.2(q, J=8Hz, 2H), 5.7(s, 2H), 7.2 (m, 2H), 7.8(m, 4H), 8.4 (m, 1H) |
| benzyl | m.p. 76–80° C. |
| 2-F-phenyl | m.p. 100–105° C. |
| 2-F, 4-F-phenyl (methyl ester) | m.p. 156–157° C. |
| 2-F, 3-F-phenyl (methyl ester) | m.p. 160–162° C. |
| 3-Cl, 4-Cl-phenyl | m.p. 138–140° C. |

EXAMPLE 12

In accordance with Example 3C, the following compounds were prepared.

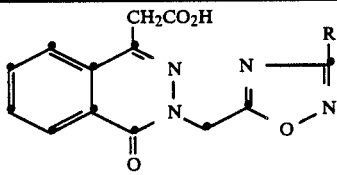

| R | M.P. °C. |
|---|---|
| 2-Cl-phenyl | 164–167 |
| phenyl | 202–205 |
| 4-Br phenyl | 193–195 |
| 2-methylphenyl | 182–184 |

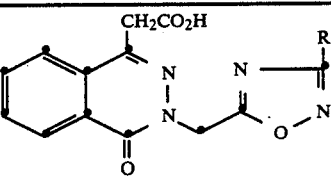

| R | M.P. °C. |
|---|---|
| 2-OCH$_3$-phenyl | 174–175 |
| 2-F, 6-Cl-phenyl | 178–182 |
| 3-Cl, 4-Cl-phenyl | 220–221 |
| 2-pyridyl | 196–200 |
| 2-Br-phenyl | 171–173 |
| benzyl | 56–60 |
| 2-F-phenyl | 210–211 |
| 2-F, 4-F-phenyl | 219–221 |
| 2-F, 3-F-phenyl | 199–200 |

EXAMPLE 13

3-(Quinolin-2-ylmethyl)-4-oxo-3H-6,7-dichlorophthalazin-1-ylacetic acid. (I; X=O; R$_1$=OH; R$_2$=quinolin-2-yl; R$_3$=R$_4$=Cl)

A. 4,5-Dichlorophthalic Anhydride

A mixture of commercially available 4,5-dichlorophthalic acid (50.4 g) and acetic anhydride (150 ml) was refluxed for 2 hours. Upon cooling the precipitate product was collected and dried in vacuum (37.0 g; m.p. 180°–181° C.).

B. 3-Ethoxycarbonylmethylidene-5,6-dichlorophthalide

A solution of 4,5-dichlorophthalic anhydride (10.0 g) and (carbethoxymethylene)triphenylphosphorane (16.0 g) in chloroform (450 ml) was refluxed for 16 hours. Evaporation of chloroform and chromatography of the residue over silica gel gave the product (9.34 g).

C. Ethyl 6,7-dichloro-4-oxo-3H-phthalazin-1-ylacetate

A mixture of 3-ethoxycarbonylmethylidene-5,6-dichlorophthalide (9.37 g), ethanol (300 ml) and hydrazine (1.1 ml) was refluxed for 3 hours. Upon cooling, the precipitated solid was collected (6.85 g.; mass spectrum, m/e 300 and 227).

The title compound was prepared from ethyl 6,7-dichloro-4-oxo-3H-phthalazin-1-ylacetate and 2-chloromethylquinoline in accordance with the procedure in Example 6, m.p. 202°–203° C.

EXAMPLE 14

3-(Quinolin-2-ylmethyl)-4-oxo-3H-phthalazin-1-ylacetic acid (I; X=O; R$_1$=OH; R$_3$=R$_4$=H; R$_2$=quinolin-2-yl)

To a solution of ethyl-4-oxo-3H-phthalazin-1-ylacetate (1.0 g) and sodium hydride (60% w/w dispersion in mineral oil) in dimethylformamide (30 ml) was added 2-bromomethylquinoline (1.05 g). The resulting solution was stirred at room temperature for 30 minutes, poured onto water (100 ml) containing 1N HCl (5 ml), and extracted with ethyl acetate. The organic extract was washed with water (3×50 ml), dried and evaporated to obtain ethyl 3-(quinolin-2ylmethyl)-4-oxo-phthalazin-1-ylacetate (1.54 g). This substance was dissolved in a water/dioxane mixture (70 ml/70 ml). To the solution was added 5N potassium hydroxide (5 ml). The solution was allowed to stir at room temperature for 15 minutes, concentrated to remove excess dioxane, diluted with water (150 ml) and extracted with ethyl acetate (3×70 ml). The aqueous layer was adjusted to pH 2 with concentrated HCl. The precipitated solid was triturated with hot ethyl acetate and then filtered to obtain the title compound (0.54 g; m.p. 193°-194° C.).

EXAMPLE 15

In accordance with Example 6, the following compounds were prepared.

TABLE 3

[Structure: isoquinoline-based ring with CH$_2$CO$_2$H group and N-N-CH$_2$-R$_2$ substituent, with ketone]

| R$_2$ | M.P. °C. |
|---|---|
| benzisothiazol-3-yl | 168 |
| 5-(2-chlorophenyl)-1,2,4-oxadiazol-3-yl | 163–165 |
| 3-phenylisothiazol-5-yl | 169–170 |
| 2-phenylisothiazol-4-yl | 218 |
| 2-phenyl-1,3,4-oxadiazol-5-yl | 260 |
| 4,5-diphenyloxazol-2-yl | 197–200 |
| quinoxalin-2-yl | 215–217 |
| N-methylbenzimidazol-2-yl | 230(d) |
| oxazolo[4,5-b]pyridine-2-yl | 228–230 |
| thiazolo[5,4-b]pyridine-2-yl | 216 |
| 5,7-dichloroquinolin-2-yl | 200–201 |
| 6-bromoquinolin-2-yl | 205–206 |
| 6,8-dichloroquinolin-2-yl | 193–195 |
| 3-methyl-1,2,5-thiadiazol-4-yl | 160–162 |
| 5-phenyloxazol-2-yl | 159–162 |
| 4-phenyloxazol-2-yl | 181–184 |
| 2-phenylthiazol-4-yl | 164–165 |
| 2-O-fluorophenylthiazol-4-yl | 184–185 |
| 4-phenylthiazol-2-yl | 181–184 |
| 5-chlorobenzothiophen-2-yl | 205–206 |
| benzothiazol-5-yl | 203–204 |
| 2-trifluoromethylbenzothiazol-5-yl | 198 |
| benzothiophen-2-yl | 192–193 |
| 6-fluorobenzothiophen-2-yl | 179–181 |
| 5-fluorobenzothiophen-2-yl | 200–201 |
| 5-nitrobenzothiophen-2-yl | 204 |
| 5-bromobenzothiophen-2-yl | 211–212 |
| 4-chlorobenzothiophen-2-yl | 204–207 |
| 3-chlorobenzothiophen-2-yl | 186–188 |
| 3-methoxybenzothiophen-2-yl | 70–73 |
| 6-bromo-3-chlorobenzothiophen-2-yl | 211–212 |
| thieno[2,3-b]pyridine-2-yl | 201–202 |
| 7-chloro-imidazo[1,5-a]pyridine-2-yl | 219–220 |
| 5-chlorobenzofuran-2-yl | 184–185 |

EXAMPLE 16

According to Example 8, the following compounds were prepared:

TABLE 4

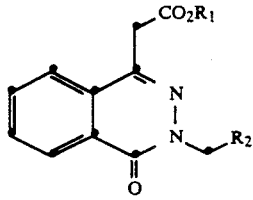

| R$_2$ | R$_1$ | Product |
|---|---|---|
| benzisothiazol-3-yl | CH$_3$ | ¹HNMR(CDCl$_3$, 60MHz): 3.7(s, 3H), 4.0(s, 2H), 5.8(s, 2H), 7.6(m, 7H), 8.3(m, 1H) |
| 3-phenylisothiazol-5-yl | C$_2$H$_5$ | m.p. 98–104° C. |
| 3-phenylisothiazol-4-yl | C$_2$H$_5$ | ¹HNMR(CDCl$_3$, 60MHz): 1.2(t, J=8Hz, 3H), 3.9 (s, 2H), 4.2(q, J=8Hz, 2H), 5.4(s, 2H)7.6 (m, 7H), 8.4(m, 1H), 8.8 (s, 1H) |
| 2-phenyl-1,3,4-oxadiazol-5-yl | C$_2$H$_5$ | ¹HNMR(CDCl$_3$, 60MHz): 1.2(t, J=8Hz, 3H), 4.0 (s, 2H), 4.2(q, J=8Hz, 2H), 5.7(s, 2H), 7.4 (m, 3H), 7.8(m, 5H), 8.4 (m, 1H) |
| 5-(2-chlorophenyl)-1,2,4-oxadiazol-3-yl | C$_2$H$_5$ | ¹HNMR(CDCl$_3$, 60MHz): 1.3(t, J=8Hz, 3H), 4.0 (s, 2H), 4.2(q, J=8Hz, 2H), 5.6(s, 2H), 7.4 (m, 3H), 7.8(m, 4H), 8.4 (m,1H) |
| N-methylbenzimidazol-2-yl | C$_2$H$_5$ | m.p. 118° C. |
| oxazolo[4,5-b]pyridine-2-yl | C$_2$H$_5$ | m.p. 105–107° C. |
| thiazolo[5,4-b]pyridine-2-yl | C$_2$H$_5$ | m.p. 111–113° C. |
| 5-phenyloxazol-2-yl | C$_2$H$_5$ | m.p. 115–117° C. |
| 4-phenyloxazol-2-yl | C$_2$H$_5$ | m.p. 130–131° C. |
| 2-phenylthiazol-4-yl | C$_2$H$_5$ | m.p. 104–106° C. |
| 2-o-fluorophenyl-thiazol-4-yl | C$_2$H$_5$ | m.p. 104–107° C. |
| 4-phenylthiazol-2-yl | C$_2$H$_5$ | m.p. 120–124° C. |
| benzothiophen-2-yl | CH$_3$ | m.p. 142–144° C. |
| 6-fluorobenzothiophen-2-yl | CH$_3$ | m.p. 118–120° C. |
| 5-fluorobenzothiophen-2-yl | CH$_3$ | m.p. 150–153° C. |
| 5-nitrobenzothiophen-2-yl | CH$_3$ | m.p. 168–170° C. |
| 5-bromobenzothiophen-2-yl | C$_2$H$_5$ | m.p. 135–136° C. |
| 4-chlorobenzothiophen-2-yl | C$_2$H$_5$ | m.p. 182–184° C. |
| 3-chlorobenzothiophen-2-yl | C$_2$H$_5$ | Not characterized; used directly in the next step. |
| 3-methoxybenzothiophen-2-yl | C$_2$H$_5$ | ¹HNMR(CDCL$_3$, 60MHz): 1.2(t, J=8Hz, 3H), 3.8 (s, 2H), 4(s, 3H), 4.1 (q, J=8Hz, 2H), 7.0–7.8 (m, 7H), 8.4–8.5(m, 1H). |
| 6-bromo-3-chlorobenzothiophen-2-yl | C$_2$H$_5$ | Not characterized; used directly in the next step. |
| thieno[2,3-b]pyridine-2-yl | CH$_3$ | m.p. 115–122° C. |
| 7-chloro-imidazo[1,5-a]pyridine-2-yl | CH$_3$ | m.p. 188–189° C. |
| 5-chlorobenzofuran-2-yl | CH$_3$ | m.p. 129–131° C. |
| Benzothiazole-5-yl | C$_2$H$_5$ | ¹NMR(CDCl$_3$, 60MHz): 1.2(t, J=8Hz, 3H), 3.9(s, 2H), 4.1(q, J= 8Hz), 7.8–8.2(m, 3H), 9.0(s, 1H). |
| 2-trifluoromethyl-benzothiazole-5-yl | C$_2$H$_5$ | m.p. 129–130° C. |
| 5-chlorobenzothio- | CH$_3$ | m.p. 139–142° C. |

TABLE 4-continued

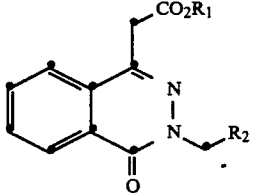

| $R_2$ | $R_1$ | Product |
|---|---|---|
| phen-2-yl | | |

EXAMPLE 17

(N-Morpholino)ethyl-3-(5,6-dichlorobenzothiazol-2-ylmethyl)-4-oxo-3H-phthalazin-1-ylacetate, hydrochloride To the sodium salt of N-2-hydroxyethylmorpholine, prepared by cautiously adding sodium hydride (0.45 g; 50% w/w/ dispersion in mineral oil) to a solution of N-2-hydroxyethylmorpholine(1.43 ml) in toluene (50 ml), was added a solution of ethyl 3-(benzothiazol-2-ylmethyl)-4-oxo-5,6-dichloro-phthalazin-1-ylacetate (1.23 g) in toluene (30 ml). After stirring the reaction mixture at room temperature for 24 hours and then at 60° C. for 6 hours, it was exposed to HCl gas and the precipitated solid was added to saturated aqueous sodium bicarbonate (100 ml) and extracted with ethyl acetate (3×100 ml). The organic layer was dried and evaporated and the resulting solid was dissolved in acetone (30 ml). Exposure of this solution to gaseous HCl gave the title compound (0.12 g), which was characterized by elemental analysis (C, 49.83%; H,3.83%; N,9.36%).

EXAMPLE 18

Sodium 3-(5-trifluoromethylbenzothiazol-2-ylmethyl)-4-oxo-3H-phthalazin-1-ylacetate Sodium methoxide (54 mg) was added to 3-(5-trifluoromethylbenzothiazol-2-ylmethyl)-4-oxo-phthalazin-1-ylacetic acid (0.4 g) in methanol 10 ml) at room temperature. After the addition was complete, a clear solution was obtained which was stirred for 15 minutes at room temperature. The excess methanol was evaporated. The residue was triturated with ether (20 ml) and filtered to obtain the product (0.43 g; m.p. 300° C.).

EXAMPLE 19

3-(5-Trifluoromethylbenzothiazol-2-ylmethyl)-4-oxo-3H-phthalazin-1-ylacetate, dicyclohexylamine salt To a mixture of 3-(5-trifluromethylbenzothiazol-2yl-methyl)-4-oxo-phthalazin-1-ylacetic acid (0.42 g) in methanol (10 ml) was added dicyclohexylamine (0.2 g) in methanol (5 ml). The resulting clear solution was stirred at room temperature for 15 minutes and then evaporated to dryness. Trituration of the residue with ether (30 ml) gave a white solid (0.38 g; m.p. 207° C.).

EXAMPLE 20

3-(5-Trifluoromethylbenzothiazol-2ylmethyl)-4-oxo-3H-phthalazin-1-ylacetic acid, meglumine salt A solution of 3-(5-trifluoromethylbenzothiazol-2-ylmethyl)-4-oxo-phthalazin-1-ylacetic acid (419 mg) and meglumine (196 mg) in methanol (50 ml) was stirred at room temperature for an hour and then evaporated to dryness. The residue was triturated with ether (25 ml), filtered and the collected solid was air dried (610 mg; m.p. 157° C.).

EXAMPLE 21

3-(5-Bromobenzothiazol-2-ylmethyl)-4-oxo-phthalazin-1-ylacetic acid, meglumine salt A solution of 3-(5 bromobenzothiazol-2-ylmethyl)-4-oxo-phthalazin-1-ylacetic acid (430 mg) and meglumine (196 mg) in methanol (50 ml) was stirred at room temperature for an hour and evaporated to dryness. The residue was triturated with ether (25 ml) and the solid collected by filtration (620 mg; m.p. 138°-140° C.).

EXAMPLE 22

Ethyl 3-5-sulfinylmethylbenzothiazole-2-ylmethyl)-4-oxo-3H-phthalazin-1-ylacetate To an ice-cold solution of ethyl-(5-thiomethylbenzothiazole-2-ylmethyl)-4-oxo-phthalazin-1-ylacetate (1.06 g) in chloroform (10 ml) was added meta-chloroperoxybenzoic acid (0.50 g). The resulting solution was stirred at between 0°-5° C. for 1 hour. The chloroform solution was washed with 10% sodium bicarbonate solution (3×20 ml) and the separated organic layer was dried over magnesium sulfate and evaporated to dryness. The residue was purified by chromatography over silica gel to obtain the title compound [0.81 g; 'HNMR (CDCl$_3$, 60 MHz): 1.2 (t, J=8 Hz, 3H), 2.65 (s, 3H), 3.95 (s, 2H), 4.1 (q, J=8 Hz, 2H), 5.75 (s, 2H), 7.4-8.3 (m, 7H)].

EXAMPLE 23

Ethyl 3-(5-sulfonylmethylbenzothiazole-2-ylmethyl)-4-oxo-3H-phthalazin-1-ylacetate A solution of ethyl-(5-thiomethylbenzothiazole-2-ylmethyl)-4-oxo-3H-phthalazin-1-ylacetate (1.06 g) and meta-chloroperoxybenzoic acid (1.3 g) in chloroform (50 ml) was stirred at room temperature for 1 hour. This solution was washed with 10% sodium bicarbonate solution (3×20 ml) and the organic extract was dried and evaporated to obtain a light yellow solid (0.85 g; 'HNMR (CDCl$_3$, 60 MHz): 1.2 (t, J=Hz, 3H), 3.1 (s, 3H), 4.0 (s, 2H), 4.15 (q, J=8 Hz, 2H), 5.85 (s, 2H), 7.4-8.3 (m, 7H).

EXAMPLE 24

Ethyl 3-(5-trifluoromethyl-2-α-methyl benzothiazolylmethyl)-4-oxo-3H-phthalazin-1-yl-acetate (; $R_1=OC_2H_5$; $R_3=R_4=H$; $R_5=CH_3$; $R_2=$ 5-trifluoromethyl-2-benzothiazolyl; $X=O$)

A. 1-(2-Benzothiazolyl)ethyl chloride

To a solution of 1-(2-benzothiazolyl)ethanol (2.5 g) prepared according to J. Indian Chem. Soc., 566 (1974) in methylene chloride (50 ml) was added thionyl chloride (3.32 g) and the resulting solution stirred at room temperature for 1 hour. The solution was poured onto ice-water (100 ml) and the organic extract separated. This extract was washed with aqueous bicarbonate (10 ml of a 5% solution) and then with water (50 ml). The methylene chloride layer was dried over anhydrous magnesium sulfate and evaporated to a light yellow oil (2.08 g).

B. 1-(5-Trifluoromethyl-2-benzothiazolyl)ethanol mesylate

To an ice-cold solution of 1-(5-trifluoromethyl-2-benzothiazolyl)ethanol (m.p. 93°-94° C., 4.94 g) in dry pyridine was added methanesulfonyl chloride (4.58 g) and the resulting solution stirred at 0° C. for 1 hour. It was poured onto water, extracted with ether and the ether layer washed with 10% hydrochloric acid (2×20 ml). The organic extract was dried, evaporated and the residue triturated with hexane to obtain the desired compound as solid, m.p. 89° C. (5.89 g).

A mixture of ethyl 4-oxo-3H-phthalazin-1-ylacetate (2.34 g) and sodium hydride (0.53 g; 50% w/w dispersion in mineral oil) in dimethylformamide (25 ml) was stirred at room temperature for 30 minutes under nitrogen. To the solution obtained was added 1-(5-trifluoromethyl-2-benzothiazolyl)ethanol mesylate (3.2 g) dissolved in dimethylformamide (5 ml), the reaction mixture stirred for an additional hour and poured onto ice-water (50 ml). The pH of the mixture was brought to 4.0 by addition of 10% hydrochloric acid (5 ml) and extracted with ethyl acetate (100 ml). The extract was washed with water (50 ml), dried over anhydrous magnesium sulfate and evaporated. The crude product was purified by chromatography over silica gel by eluting with ethylacetate-chloroform (5/95% mixture). The title compound (2.0 g) was obtained by evaporation of eluants, m.p. 105°-106° C.

EXAMPLE 25

3-(Benzothiazole-5-ylmethylbenzothiazolyl)-4-oxo-3H-phthalazin-1-ylacetic acid

A. 5-Bromomethylbenzothiazole was prepared according to Example 1C starting from 5-methylbenzothiazole made according to Grazz. Chim. Ital., 95, 499 (1965). The products showed the following NMR resonances - TMS (60 MHz, CDCl$_3$) 4.6 (s,2H), 7.4 (dd, 1H,J=10 Hz, J=2 Hz),7.85 (d, 1H,J=10 Hz), 8.15(d,J=2 Hz), 9.0(s,1H).

B. Ethyl 3-(5-methylbenzothiazolyl)-4-oxo-3H-phthalazin-1-yl-acetate prepared according to Example 1D had the following NMR resonances - TMS, (60 MHz, CDCl$_3$) 1.2(t,J=8 Hz,3H),3.95(s,2H),4.2(q,J=8 Hz,2H),5.6 (s,2H),7.2-8.2(m,7H),9.0(s,1H).

C. The title compound was prepared according to Example 1E, m.p. 203°-204° C.

EXAMPLE 26

Ethyl-3-(5-fluorobenzothiazolyl-2-ylmethyl)-4-oxo-3H-phthalazin-ylacetate

To a mixture of ethyl 4-oxo-3H-phthalazin-1-ylacetate (2.34 g) in dimethylformamide (15 ml) was added sodium methoxide (0.51 g). To the clear yellow solution obtained upon stirring the mixture for 5 minutes was added a solution of 5-fluoro-2-chloromethylbenzothiazole made in accordance with Example 1C in dimethylformamide (5 ml). After stirring the resulting solution for 1 hour, it was poured onto ice-water (50 ml) and extracted with methylene chloride. Evaporation of the organic extract gave a light orange colored solid, which was crystallized from ethanol to obtain the title compound (3.84 g, m.p. 118°-120° C.).

EXAMPLE 27

A. Ethyl-3-cyanomethyl-4-oxo-3H-phthalazin-1-ylacetate

To a solution of ethyl-4-oxo-3H-phthalazin-1-yl acetate (11.31 g) and dry potassium t-butoxide (5.9 g) in dimethylformamide (50 ml) was added chloroacetonitrile (3.78 g) and the solution was stirred for 30 minutes. This solution was poured onto ice water (300 ml); sufficient 10% HCL was added to adjust the pH of the resulting mixture to about 4.0 and the precipitated solid was collected and air-dried (yield: 11.81 g; m.p. 113°-114° C.).

B. Ethyl-3 5,7-difluorobenzothiazol-2-ylmethyl)-4-oxo-3H-phthalazin-1-ylacetate A mixture of ethy-3-cyanomethyl-4-oxo-3H-phtnalazin-1-ylacetate (1.29 g), 2-amino-4,6-difluorothiophenol hydrochloride (0.98 g) and ethanol (20 ml) was refluxed for 6 hours. Upon cooling, the title compound precipitated out as a pale yellow solid (yield: 1.62 g; m.p. 115°-117° C.).

Ethyl-3-(5-methoxybenzothiazol-2-ylmethyl)-4-oxo-3H-phthalazin-1-ylacetate (m.p. 127°-129° C.), ethyl-4-trifluoromethyl-2-ylmethyl)-4-oxo-3H-phthalazin-1-ylacetate (m.p. 136°-138° C.) and ethyl-3-(5,7-bistrifluoromethylbenzothiazol-2-ylmethyl)-4-oxo-3H-phthalazin-1-ylacetate (m.p. 124°-126° C.) were also prepared by the above procedure starting from appropriately substituted amino-thiophenol hydrochlorides.

EXAMPLE 28

3-(5,7-Dihydroxy-2-benzothiazolylmethyl)-4-oxo-3H-phthalazin-1-ylacetic acid

A mixture of 3-(5,7-dimethoxy-2-benzothiazolylmethyl)-4-oxo-3H-phthalazin-1-yl acetic acid (0.5 g) and aqueous hydrobromic acid (10 ml, 48%) was refluxed for 4 hours. The hot solution was cooled to room temperature and than poured onto ice-water (50 ml). The resulting pink colored solid was filtered, washed with water (20 ml) and dried. The dried solid was crystallized from methanol to yield the product (0.31 g; m.p. 184° C.).

3-(4-Hydroxy-2-benzothiazolylmethyl)-4-oxo-3H-phtnalazin-1-ylacetate acid (m.p. 154°-156° C.) was similarly prepared starting from 3-(4-methoxy-2-benzozolylmethyl)-4-oxo-3H-phthalazin-1-ylacetic acid.

EXAMPLE A

In Table 5, the first two intermediates were prepared by the method of U.S. Pat. No. 4,251,528 and the remaining intermediates by the method of Example 13C.

TABLE 5

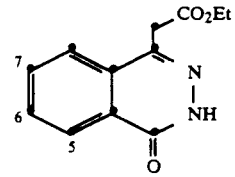

| Substituent | Product |
| --- | --- |
| 5-F | U.S. Pat. No. 4,251,528 |
| 5-CH$_3$ | U.S. Pat. No. 4,251,528 |
| 7-Cl | m.p. 189-190° C. |
| 6-Cl, 7-Cl | m.p. 250° C. |

TABLE 5-continued

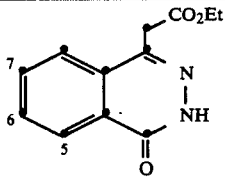

| Substituent | Product |
|---|---|
| 6-NO$_2$ | m.p. 224–225° C. |
| 7-CH$_3$ | m.p. 228–230° C. |
| 7-OCH$_3$ | m.p. 231–232° C. |
| 7-NO$_2$ | m.p. 172–174° C. |
| 6-isopropyl | TMS(300MHz, CDCl$_3$): 8.28 (s, 1H), 7.63(d, J=3Hz, 2H), 4.12(q, J=9Hz, 2H), 3.92(s, 2H), 3.04(sep., J=9Hz, 1H), 1.25(d, J=9Hz, 6H), 1.16(t, J=6Hz, 3H) |
| 7-isopropyl | TMS(300MHz, CDCl$_3$): 8.32(d, J=9Hz, 1H), 7.65(dd, J=1Hz, 9Hz, 1H), 7.55(s, 1H), 4.15 (q, J=9Hz, 2H), 3.96(s, 2H), 3.06(sep., J=9Hz, 1H), 1.27 (d, J=9Hz, 6H), 1.18(t, J=6Hz, 3H) |

TABLE 5-continued

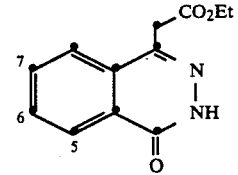

| Substituent | Product |
|---|---|
| 6-CF$_3$ | TMS(90MHz, DMSO-d6): 13.0–12.6(br, 1H), 8.4(s, 1H), 8.2–79(m, 2H), 4.00(q, J=9Hz, 2H), 3.98(s, 2H), 1.0(t, J=9Hz,3H) |
| 7-CF$_3$ | TMS(90MHz, DMSO-d6): 13.0–12.6(br, 1H), 8.5(d, J=9Hz, 1H), 8.22(m, 1H), 8.1(s, 1H), 4.10(1, J=9Hz, 2H), 4.10(s, 2H), 1.15(t, J=9Hz, 3H) |

EXAMPLE B

The following intermediates were prepared according to Example 1C unless otherwise indicated. All melting points are in degrees Centigrade.

TABLE 6

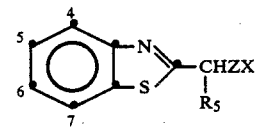

| Substituent | R$_5$ | Z | X | Product |
|---|---|---|---|---|
| 6-Cl | H | — | Br | $^1$HNMR(CDCl$_3$, 60MHz): 4.75(s, 2H), 7.35(dd, J=2, 8Hz, 1H), 7.75(d, J=2.8Hz, 1H), 7.85(d, J=8Hz, 1H) |
| 5-Br | H | — | Br | m.p. 107 |
| 6-Br | H | — | Br | m.p. 108 |
| 7-Br | H | — | Br | $^1$HNMR(CDCl$_3$, 60MHz): 4.7(s, 2H), 7.2–8.0(m, 3H) |
| 5-Cl, 6-Cl | H | — | Br | $^1$HNMR(CDCl$_3$, 90MHz): 4.80(s, 2H), 8.00(s, 1H), 8.15(s, 1H) |
| 4-Cl, 6-Cl | H | — | Br | m.p. 131–134 $^1$HNMR(CDCl$_3$, 90MHz): 4.80(s, 2H), 7.45(d, J=1Hz), 7.65(d, J=1Hz, 1H) |
| 6-OCH$_3$ | H | — | Br | $^1$HNMR(CDCl$_3$, 90MHz): 3.85(s, 3H), 4.75(s, 2H), 7.05(dd, J=2, 9Hz, 1H), 7.25(d, J=2Hz, 1H), 7.85(d, J=9Hz, (1H) |
| 6-CH$_3$ | H | — | Br | $^1$HNMR(CDCl$_3$, 90MHz): 2.45(s, 3H) 4.90(s, 2H), 7.25(d, J=7Hz, 1H), 7.60(s, 1H), 7.85(d, J=8Hz, 1H) |
| 5-Cl | H | — | Cl | m.p. 78–80 |
| 4-Cl* | H | — | Cl | m.p. 114–115 |
| 4-F* | H | — | Cl | $^1$HNMR(60MHz, CDCl$_3$): 4.9(s, 2H), 7.0–79(m, 3H) |
| 4-F, 5-F* | H | — | Cl | m.p. 68–70 |
| 5-F, 7-F | H | — | Cl | m.p. 53–54 |
| 5-Cl, 7-Cl* | H | — | Cl | m.p. 74–76 |
| 4-Cl, 5-Cl | H | — | Cl | $^1$HNMR(60MHz, CDCl$_3$): 4.7(s, 2H), 6.6(d2H, J=10Hz), 7.2(d, 2H, J=10Hz) |
| 4-Cl, 7-Cl | H | — | Cl | m.p. 134–135 |
| 5-CH$_3$ | H | — | Cl | m.p. 114–116 |
| 6-isopropyl | H | — | Cl | $^1$HNMR(90MHz, CDCl$_3$): 7.85(d, J=9Hz, 1H), 7.65(d, J=3Hz, 1H), 7.40(dd, J=3Hz, 9Hz, 1H), 4.9(s, 2H), 3.00(sep., J=6Hz, 1H)1.35(d, J=6Hz, 6H) |
| H | CH$_3$ | — | Cl | $^1$HNMR(60MHz, CDCl$_3$): 2.0(d, 3H, J=8Hz), 5.4(q, 1H, J=8Hz), 7.0–8.0(m, 4H) |
| 4-OCH$_3$ | H | — | Cl | NMR(60MHz, CDCl$_3$), 3.45 (s, 3H), 4.85(s, 2H), 5.5–7.2(m, 3H) |

TABLE 6-continued

[Structure: benzothiazole with positions 4,5,6,7 and =N-CHZX with R5 substituent]

| Substituent | R5 | Z | X | Product |
|---|---|---|---|---|
| 5-OCH3, 7-OCH3 | H | — | Cl | m.p. 105 |
| 6-CF3 | H | — | Cl | m.p. 47–49* |
| 5-CF3 | CH3 | — | OSO2CH3 | m.p. 84 |
| 5-Cl | CH3 | — | OSO2CH3 | m.p. 92–94 |
| H | H | S | Cl | 'HNMR(60MHz, CDCl3): 5.25(s, 2H), 7.0–8.0(m, 4H) |
| 5-Cl | H | S | Cl | 'HNMR(60MHz, CDCl3): 5.25(s, 2H), 7.0–8.0(m, 3H) |

*Prepared according to Can. J. Chem., 43, 2610 (1965)

EXAMPLE C

The following intermediates were prepared by the indicated methods of the prior art, or by the method of Example 1B.

TABLE 7

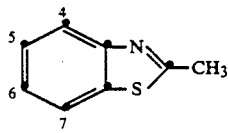

| Substituent | Product |
|---|---|
| 5-bromo | Chemical Abstracts; 1957 52,6319 |
| 6-bromo | J. Chem. Soc.; 1936, 1225 |
| 7-bromo | Liquid; m/e 228 |
| 5-Cl, 6-Cl | m.p. 134–135° C. |
| 6-CH3 | Prepared similarly to procedures in J. Chem. Soc.; 1922, 1493 and J. Org. Chem.; 1976, 41, 776 |
| 4-Cl, 6-Cl | Synthesis; 1976, 730 |
| 6-Cl | Synthesis; 1976, 730 |

EXAMPLE D 5-(2-Chlorophenyl)-2-chloromethyl-1,2,4-oxadiazole

A. O-2-Chlorobenzoyl-chloroacetamidoxime

Chloracetamidoxime (5 g) was dissolved in warm benzene (20 ml) and 2-chlorobenzoyl chloride (6.4 ml) was cautiously added to it. The resulting mixture was heated at 40° C. for 30 minutes and excess benzene was removed. After cooling to room temperature the soldifed mass was triturated with cold benzene and filtered to obtain the compound (1.6 g; m.p. 126°–130° C.).

B. O-2-chlorobenzoyl-chloroacetamidoxime (1.4 g) was added to refluxing diglyme (10 ml) and the refluxing continued for 10 minutes. After cooling, the reaction mixture was poured onto water (20 ml) containing ether (50 ml). The ether layer was washed with water (2×50 ml), saturated aqueous sodium bicarbonate (2×10 ml) and the organic layer dried and evaporated. The residue was chromatographed over silica gel to obtain the product, 0.8 g of a colorless oil, 'HNMR(CDCl3,60 MHz): 4.7 (s,2H), 7.45 (m, 3H), 8.1 (m, 1H).

EXAMPLE E

The commercially available 2-amino-3-hydroxypyridine (5.0 g) and diglyme (30 ml) were heated at 125° C. to obtain a solution. To this solution was added 2-chloro-1,1,1-triethoxyethane (9.9 g) and the resulting mixture held at 125° for 1 hour. The solution was cooled to room temperature and then decanted to remove a black byproduct residue. The filtrate was diluted with water (50 ml) and the resulting yellow precipitated 2-chloromethyl-oxazolo[4,5-b]pyridine was collected (1.5 g). A small sample was crystallized from isopropanol (m.p. 115°–118° C.).

2-Chloromethyl-thiazolo[5,4-b]pyridine was prepared similarly by heating a mixture of 3-amino-2-mercaptopyridine (3.6 g), 2-chloro-1,1,1-triethoxyethane (6.5 g) and ethanol (60 ml) at 60° C. for 4 hours. The crude solid resulting from evaporation of ethanol was chromatographed over silica gel to obtain 2.94 g of the product, m.p. 71°–73° C.

Similarly, 2-chloromethyl-5-trifluoromethylbenzothiazole, m.p. 52°.C., was formed from 2-amino-4-trifluoromethylthiophenol hydrochloride and 2-chloro-1,1,1-triethoxyethane in ethanol.

EXAMPLE F

Intermediates of the formula Hal—$CH_2R_2$ were prepared by the methods listed below or by the method of Example E or by the procedure of J. Chem. Soc. (C), 731 (1967) indicated by an asterisk (*).

TABLE 8

| Structure | Product |
|---|---|
| 3-bromomethylbenzisothiazole | R. A. Gillham, Jr., Ph.D. thesis, California Institute of Technology, 1969 |
| 3-phenyl-5-chloromethyl-isothiazole | 'HNMR(CDCl3, 60MHz): 4.8(s, 2H), 7.4(m, 3H), 7.9(m, 2H) |
| 2-chloromethyl-5-phenyl-oxazole | m.p. 64–66° C. |
| 2-chloromethyl-4-phenyl-oxazole | m.p. 50–52° C. |
| 5-chloromethyl-2-phenyl-thiazole | U.K. Patent 1,137,529 |
| 5-chloromethyl-2-0-fluoro-phenylthiazole | U.K. Patent 1,137,529 |
| 3-phenyl-4-chloromethyl-isothiazole | 'HNMR(CDCl3, 60MHz): 4.5(s, 2H), 7.4(m, 3H), 7.7(m, 2H) |
| 2-phenyl-5-chloromethyl-1,3,4-oxadiazole | Chem. Ber. 96, 1049 (1963) |
| *2-chloromethyl-5-chloro-benzothiophene | J. Chem. Soc. (C), 731 (1967) |
| 3-chloromethyl-5-(2-chloro-phenyl)1,2,4-oxadiazole | Prepared similarly to procedure in J. Heterocyclic Chem. 16, 1469 (1979). 'HNMR (CDCl3, 60MHz): 4.7 |

TABLE 8-continued

| Structure | Product |
|---|---|
| | (s, 2H), 7.45(m, 3H), 8.1 (m, 1H) |
| N-methyl-2-chloromethyl-benzimidazole | JACS, 65, 1854, (1943), m.p. 95° C. |
| 3-methyl-4-bromomethyl-1,2,5-thiadiazole | J. Heterocyclic Chem., 21, 1157 (1984), b.p. 30–35° C. at 7 mm |
| 2-Chloromethylbenzothiophene | J. Chem. Soc. (C), 731 (1967) |
| *2-chloromethyl-5-fluorobenzothiophene | m.p. 37–40° C. |
| *2-chloromethyl-5-nitrobenzothiophene | m.p. 95–99° C. |
| *2-chloromethyl-5-bromobenzothiophene | m.p. 65–67° C. |
| *2-chloromethyl-4-chlorobenzothiophene | m.p. 63–65° C. |
| *2-bromomethyl-3-chlorobenzothiophene | 'HNMR(CDCl$_3$, 60MHz): 4.6(s, 2H), 7.2–7.8 (m, 4H) |
| *2-bromomethyl-3-methoxybenzothiophene | 'HNMR(CDCl$_3$, 60MHz): 4.0(s, 3H), 5.0(s, 2H), 7.2–7.8(m, 4H) |
| 2-chloromethyl-6-bromo-3-chlorobenzothiophene | 'HNMR(CDCl$_3$, 60MHz): 4.65(s, 2H), 7.45 (s, 2H), 7.8(s, 1H). [Prepared according to J. Med. Chem. 29, 1643 (1986)] |
| 2-chloromethylthieno[2,3-b]pyridine | m.p. 47–49° C. |
| 2-chloromethyl-7-chloro-imidazo[1,2-a]pyridine | Prepared according to Il Farmaco-Ed. Sc., 815 (1975), m.p. 122–124° C. |
| 2-chloromethyl-5-chloro-benzofuran | 'HNMR(CDCl$_3$, 60MHz): 4.6 (s, 2H), 6.5(s, 1H), 6.8–7.5(m, 3H) |

EXAMPLE G

The benzoate of 4-phenylthiazole-2-methanol (7.4 g), prepared according to J. Am. Chem. Soc., 53, 1470 (1931) was dissolved in anhydrous tetrahydrofuran (50 ml). To this solution was added lithium aluminum hydride (525 mg) and the mixture stirred for one hour at room temperature. After carefully quenching the excess lithium aluminum hydride with ethyl acetate, the mixture was poured onto ice-cold water (50 ml) and acidified to pH 3 using 10% HCl. The mixture was filtered and the filtrate was extracted with ether (3×50 ml). The organic extract wad dried, evaporated and the crude product was purified by chromatography to obtain 4-phenylthiazole-2-methanol (1.8 g). This compound was converted to 4-phenylthiazole-2-methanol, methane sulfonate according to the procedure described in Example 24B. The melting point of the product was 80° C.

EXAMPLE H

The following intermediates were prepared by the method of Helvitica Chimica Acta 49, 412 (1966) except for the last two intermediates which were prepared by the method of J. Med. Chem. 4,351 (1961).

TABLE 9

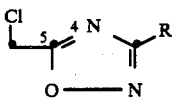

| R | Product |
|---|---|
| phenyl | Helvitica Chimica Acta |

TABLE 9-continued

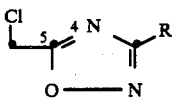

| R | Product |
|---|---|
| | 49, 412 (1966) |
| 2-Cl phenyl | 'HNMR(CDCl$_3$, 60MHz): 4.8(s, 2H), 7.4(m, 3H), 7.9(m, 1H) |
| 4-Br phenyl | m.p. 155–160° C. |
| 2-methylphenyl | 'HNMR(CDCl$_3$, 60MHz): 2.6(s, 3H), 4.7(s, 2H), 7.3(m, 3H), 8.0(m, 1H) |
| 2-OCH$_3$ phenyl | m.p. 59–62° C. |
| 2-F, 6-Cl phenyl | 'HNMR(CDCl$_3$, 60MHz): 4.8(s, 2H), 7.3(m, 3H) |
| 2-F-phenyl | m.p. 32–34° C. |
| 2-F, 4-F-phenyl | m.p. 34–35° C. |
| 2-F, 3-F-phenyl | m.p. 40–42° C. |
| 3-Cl, 4-Cl phenyl | m.p. 38–41° C. |
| 2-pyridyl | m.p. 89–94° C. |
| 2-bromophenyl | m.p. 45–46° C. |
| 2-CF$_3$ phenyl | 'HNMR(CDCl$_3$, 60MHz): 4.8(s, 2H), 7.8(m, 4H) |
| benzyl | 'HNMR(CDCl$_3$, 60MHz): 4.0(s, 2H), 4.4(s, 2H), 7.3(s, 5H) |

EXAMPLE J

A mixture of 5-chloro-2-hydroxyaniline (10 g), chloroacetamidic acid ethyl esterhydrochloride (8.5 g) in chloroform (100 ml) was refluxed for 5 hours. The dark brown solution was filtered, washed first with 10% aqueous potassium hydroxide solution (10 ml) and then water (20 ml). The organic layer was dried (magnesium sulfate) and then evaporated to dryness. The residue was purified by column chromatography (m.p. 53°–56° C., yield, 8.6 g).

The following intermediates were prepared by the above procedure.

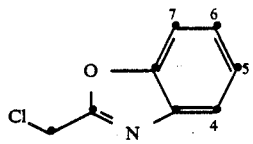

| Substituent | Product |
|---|---|
| 5-bromo | m.p. 63–65° C. |
| 5-Cl, 7-Cl | m.p. 52–53° C. |
| 5,6-dibenzo | m.p. 105° C.(d) |
| 5-F, 7-F | m.p. 118–121° C. |
| 5-CF$_3$ | m.p. 50–54° C. |

EXAMPLE K

The following intermediates were prepared from commercially available appropriately substituted anilines following the procedure described in U.S. Pat. No. 4,052 379.

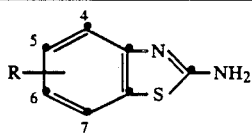

| R | Product identification |
|---|---|
| 5,7-difluoro (hydrobromide salt) | m.p. 283-284° C. |
| 5,7-dimethoxy (hydrobromide salt) | 270° C. |
| 5-trifluoromethyl | U.S. Pat. No. 4,052,379 |
| 5,7-bistrifluoromethyl | m.p. 201-202° C. |

EXAMPLE L

The following intermediates were prepared from the following starting materials following the procedure described in Synthetic Communications, 10,167 (1980).

| Intermediates | Starting materials |
|---|---|
| 2-amino-3-trifluoromethyl-thiophenol (m.p. 211-213° C.) | 4-trifluoromethylbenzo-thiazole |
| 2-amino-5-trifluoromethyl-thiophenol hydrochloride (m.p. 210-213° C.) | 5-trifluoromethyl-benzothiazole |
| 2-amino-4,6-bistrifluoro-methylthiophenol hydrochloride (m.p. 229-230° C.) | 4,6-bistrifluoromethyl-benzothiazole |
| 4-trifluoromethylbenzo-thiazole (m.p. 47-48° C.) | 2-amino-4-trifluoro-methylbenzothiazole |
| 5-trifluoromethylbenzo-thiazole (m.p. 42° C.) | 2-amino-5-trifluoro-methylbenzothiazole |
| 5,7-bistrifluoromethylbenzo-thiazole (m.p. 64-66° C.) | 2-amino-5,7-bistrifluoro-methylbenzothiazole |

EXAMPLE M

5-Bromomethylbenzothiazole

A mixture of 5-methylbenzothiazole (5.0 g), N-bromosuccinimide (6.0 g) and carbon tetrachloride (500 ml) was refluxed for 4 hours. Upon cooling, the mixture was evaporated to dryness and the residue chromatographed over silica gel. On elution with a mixture of methylene chloride and hexane (9:1), the title product was obtained as a white solid [0.56 g; NMR(CDCl$_3$,60 MHz): 4.6 (s, 2H), 7.4 (dd, J=7 Hz, 2 Hz, 1H). 7.9 (d, J=7 Hz, 1H), 8.15 (d, J=2 Hz, 1H), 9.0 (s, 1H).

2-Trifluoromethyl-5-bromomethylbenzathiazole was prepared according to the above procedure starting from 2-trifluoromethyl-5-methylbenzothiazole [(NMR, CDCl$_3$), 4.6 (s, 2H), 7.5 (dd, J=7 Hz, 2 Hz, 1H), 7.9 (d, J=7 Hz, 1H), 8.1 (d, J=2 Hz)].

EXAMPLE N

2-Chloromethyl-thieno[2,3-b]pyridine

Thieno[2,3-b]pyridine-2-carboxaldehyde (1.63 g) prepared according to J. Het. Chem. 355 (1974) was dissolved in ethanol (20 ml) and to the solution was added sodium borohydride (0.19 g). After 30 minutes the solution was evaporated to dryness and the residue extracted with methylene chloride (50 ml). The organic extract was washed with water (2×25 ml), the extract dried and then evaporated to obtain 2-hydroxymethyl-thieno[2,3-b]pyridine (1.40 g) as an amber oil. 'HNMR (CDCl$_3$,60 MHz): 4.9 (s, 1H), 6.3 (s, 1H), 6.9 s, 1H), 7.1 (m, 1H), 7.8 (m, 1H), 8.4 (m, 1H). This product was dissolved in a solution of pyridine (2 ml) in methylene chloride (20 ml) and to the resulting solution was added methane sulfonyl chloride (1.14 g). Upon stirring overnight at room temperature, the solution was poured onto ice water (25 ml). The methylene chloride layer was separated, washed with water (2×10 ml) and then dried and evaporated. The residue was purified by chromatography on silica gel with a mixture of methylene chloride-ethyl acetate (9:1) as eluant to obtain the title compound (0.76 g; m.p. 47°-49° C.).

EXAMPLE O

2-Bromomethyl-3-methoxy-benzothiophene

To a solution of 3-methoxybenzothiophene-2-carboxaldehyde [3.4 g; J. Chem. Soc. C 779 (1967)] in ethanol (60 ml) was added sodium borohydride (0.34 g). After 10 minutes the solution was poured onto water (200 ml) and extracted with ether (2×50 ml). The ether extracts were washed with water (2×25 ml), dried and then evaporated to the title product as an orange oil. Yield, 3.4 g. 'HNMR (CDCl$_3$, 60 MHz): 2.6 (s, 1H), 3.8 (s, 3H), 4.8 (s, 2H), 7.0-8.0 (m, 4H). This material (1.5 g) was dissolved in ether (20 ml). To the solution cooled in an ice-bath was added phosphorous tribromide (0.7 ml). The mixture was let to stand for 1 hour. The reaction mixture was poured onto ice-water (50 ml) and the ether layer separated, collected, dried and evaporated to obtain the title product as a light yellow oil (yield, 1.4 g). 'HNMR CDCl$_3$, 60 MHz): 4.0 (s, 3H), 5.0 (s, 2H), 7.2-7.8 (m, 4H).

EXAMPLE P

To a suspension of ethyl-5-chloro-benzofuran carboxylate (1.05 g), prepared according to Helv. Chim. Acta., 818 (1935), in tetrahydrofuran (10 ml) was added lithium aluminum hydride (0.1 g). The mixture was stirred at room temperature for 1 hour. Ethyl acetate (50 ml) was slowly added to the reaction mixture, and the whole mixture was poured onto water (50 ml). The organic extract was separated, washed with water (2×25 ml), dried and evaporated to obtain 2-hydroxymethyl-5-cnlorobenzofuran as an oil [0.87 g; 'HNMR (CDCl$_3$, 60 MHz): 4.6 (s, 2H), 6.6-7.4 (m, 4H)]. This material was added to a solution of methanesulfonyl chloride (1.15 g) in methylene chloride (20 ml) containing pyridine (1 ml). After stirring the reaction overnight it was poured onto ice-water (20 ml) and the organic extract was first washed with 10% HCl (5 ml) and then with water (2×10 ml). The washed extract was dried and evaporated to obtain 2-chloromethyl-5-chlorobenzofuran as a clear oil (yield: 0.5 g); HNMR (CDCl$_3$, 60 MHz): 4.65 (s, 2H), 6.6 (s, 1H), 6.8-7.4 (m, 3H).

We claim:
1. A compound of the formula

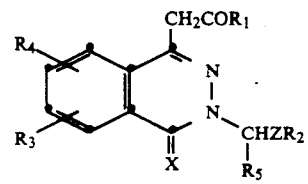

wherein
X is oxygen or sulfur;
Z is a covalent bond, O, S, NH or CH$_2$, or CHR$_5$Z is vinylene;

$R_1$ is hydroxy, or a prodrug group;

$R_2$ is a heterocyclic 5-membered ring having one nitrogen, oxygen or sulfur, two nitrogens one or which may be replaced by oxygen or sulfur, or three nitrogens one of which may be replaced by oxygen or sulfur, said heterocyclic 5-membered ring substituted by one or two fluoro, chloro, ($C_1$–$C_4$)alkyl or phenyl, or condensed with benzo, or substituted by one of pyridyl, furyl or thienyl, said phenyl or benzo optionally substituted by one of iodo, cyano, nitro, perfluoroethyl, trifluoroacetyl, or ($C_1$–$C_4$)alkanoyol, one or two of fluoro, chloro, bromo, hydroxy, ($C_1$–$C_4$)alkyl, ($C_1$–$C_4$)alkoxy, ($C_1$–$C_4$)alkylthio, trifluoromethoxy, trifluoromethylthio, ($C_1$–$C_4$)alkylsulfinyl, ($C_1$–$C_4$)alkylsulfonyl, or trifluoromethyl, or two fluoro or two trifluoromethyl with one hydroxy or one ($C_1$–$C_4$)alkoxy, or three fluoro, said pyridyl, furyl or thienyl optionally substituted in the 3-position by fluoro, chloro bromo, ($C_1$–$C_4$)alkyl or ($C_1$–$C_4$)alkoxy;

a heterocyclic 6-membered ring having two or three nitrogen atoms or one or two nitrogen atoms and one oxygen or sulfur, said heterocyclic 6-membered ring substituted by one or two ($C_1$–$C_4$)alkyl or phenyl, or condensed with benzo, or substituted by one of pyridyl, furyl or thienyl, said phenyl or benzo optionally substituted by one of iodo or trifluoromethylthio, or one or two of fluoro, chloro, bromo, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl, or trifluoromethyl, and said pyridyl, furyl or thienyl optionally substituted in the 3-position by fluoro, chloro, ($C_1$–$C_4$)alkyl or ($C_1$–$C_4$)alkoxy;

said benzo-condensed heterocyclic 5-membered or 6-membered rings optionally substituted in the heterocyclic 5-membered or 6-membered ring by one of fluoro, chloro, bromo, methoxy, or trifluoromethyl;

oxazole or thiazole condensed with a 6-membered aromatic group containing one or two nitrogen atoms, with thiophene or with furane, each optionally substituted by one of fluoro, chloro, bromo, trifluoromethyl, methylthio or methylsulfinyl;

imidazolopyridine or triazolopyridine optionally substituted by one of trifluoromethyl, trifluoromethylthio, bromo, or ($C_1$–$C_4$)alkoxy, or two of fluoro or chloro;

thienothiophene or hienofuran optionally substituted by one of fluoro, chloro or trifluoromethyl;

thienotriazole optionally substituted by one of chloro or trifluoromethyl;

naphthothiazole; naphthoxazole; or thienoisothiazole;

$R_3$ and $R_4$ are the same or different and are hydrogen, fluoro, chloro. bromo, trifluoromethyl, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsufonyl, or nitro, or $R_3$ and $R_4$ taken together are ($C_1$–$C_4$)alkylenedioxy; and $R_5$ is hydrogen methyl or trifluoromethyl; or a pharmaceutically acceptable base addition salt of a compound of formula I wherein $R_1$ is hydroxy, or an acid addition salt of a compound of formula I wherein $R_1$ is di($C_1$–$C_4$)alkylamino or ($C_1$–$C_4$)alkoxy substituted by N-moropholino or di($C_1$–$C_4$)alkylamino.

2. A compound according to claim 1 wherein X is oxygen.

3. A compound according to claim 1 wherein $R_2$ is optionally substituted benzothiazolyl or benzoxazolyl, or substituted oxadiazolyl.

4. A compound according to claim 1 wherein $R_2$ is optionally substituted isoquinolyl, benzothiophen-yl, benzofuran-yl or benzimidazolyl, or substituted indolyl.

5. A compound according to claim 1 wherein X is oxygen, Z is a covalent bond, $R_1$ is hydroxy, $R_2$ is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, benzothiophen-2-yl, benzofuran-2-yl, thiazolo[4,5-b]pyridine-2-yl, thieno[2,3-b]pyridine-2-yl, imidazo[1,5-a]pyridine-2-yl, or indol-2-yl, or substituted 1,2,4- oxadiazol-3-yl, 1,2,4-oxadiazol-5-yl, isothiazol-5-yl, isothiazol-4-yl, 1,3,4-oxadiazol-5-yl, 1,2,5-thiadiazol-3-yl, oxazol-2-yl, thiazol-2-yl, or thiazol-4-yl, and $R_3$, $R_4$ and $R_5$ are hydrogen.

6. A compound according to claim 1 wherein X is oxygen, Z is a covalent bond, $R_1$ is hydroxy, $R_2$ is optionally 4,5,6 or 7 benzo-substituted benzothiazolyl, benzoxazolyl, benzimidazolyl, benzothiophenyl, benzofuranyl, or indolyl.

7. A compound according to claim 1 wherein $R_2$ is 2-benzothiazolyl substituted in the benzo by one trifluoroacetyl, or trifluoromethylthio, or one or two of fluoro, chloro, bromo, hydroxy, methyl, methoxy, trifluoromethyl, trifluoromethoxy, trifluoromethylthio, or two fluoro or two trifluoromethyl with one methoxy, or three fluoro, or by 6,7-benzo.

8. A compound according to claim 1 wherein $R_3$ is hydrogen, 5-fluoro, 5-chloro, 5-bromo or 5-methyl, and $R_4$ is hydrogen, 6- or 7- substituted chloro, bromo, methyl, isopropyl, methoxy, nitro or trifluoromethyl; or $R_3$ and $R_4$ is 4,5-difluoro.

9. A compound according to claim 1 wherein $R_2$ is optionally substituted benzothiazol-2-yl or quinoxalyl, and $R_3$ and $R_4$ are each chloro.

10. A compound according to claim 1 wherein X is oxygen, Z is a covalent bond, $R_1$ is hydroxy, $R_3$, $R_4$ and $R_5$ are hydrogen, and $R_2$ is 5-bromo-2-benzothiazolyl, 5-fluoro-2-benzothiazolyl, 5-trifluoromethyl-2-benzothiazolyl, 5-chloro 2-benzothiazolyl, 4,5-difluoro-2-benzothiazolyl, 5,7-difluoro-2-benzothiozolyl, 4,7-dichloro-2-benzothiazolyl, 5,7-dichloro-2-benzothiazolyl, or 5,7-bistrifluoromethyl-2-benzothiazolyl.

11. A compound according to claim 10 in the form of the sodium salt or the N-methylglucamine salt.

12. A compound according to claim 1 wherein X is oxygen, Z is a covalent bond, $R_1$ is hydroxy, $R_2$ is optionally substituted benzothiazol-2-yl, $R_3$ and $R_4$ are hydrogen, and $R_5$ is methyl.

13. A compound according to claim 1 wherein X is oxygen, Z is a covalent bond, $R_1$ is hydroxy, $R_3$, $R_4$ and $R_5$ are hydrogen, and $R_2$ is optionally 4, 5, 6 or 7 benzo-substituted 2-trifluoromethyl-benzothiazolyl, 2-trifluoromethyl-benzoxazolyl, 2-trifluoromethyl-benzimidazolyl, 2-trifluoromethyl-benzofuran, 3-trifluoromethyl-benzofuran, 2-trifluoromethyl-benzothiophen, 3-trifluoromethyl-benzothiophen, 2-trifluoromethyl-indolyl, or 3-trifluoromethyl-indolyl.

14. A compound according to claim 1 wherein X is oxygen, Z is $CH_2$, $R_1$ is hydroxy, $R_2$ is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, or thiazolo[4,5-b]pyridine-2-yl, or substituted 1,2,4- oxadiazol-3-yl, 1,2,4-oxadiazol-5-yl, isothiazol-5-yl, isorhiazol-4-yl, 1,3,4- oxadiazol-5-yl, 1,2,5-thiadiazol-3-yl, oxazol-2-yl, thiazol-2-yl, or thiazol-4-yl, and $R_3$, $R_4$ and $R_5$ are hydrogen.

15. A composition for inhibition of aldose reductase activity comprising a compound of claim 1 in an amount effective in the inhibition of aldose reductase activity, in admixture with a pharmaceutically acceptable carrier.

16. A composition according to claim 15 wherein X is oxygen.

17. A composition according to claim 15 wherein $R_2$ is optionally substituted benzothiazolyl or benzoxazolyl, or substituted oxadiazolyl.

18. A composition according to claim 15 wherein $R_2$ is optionally substituted isoquinolyl, benzothiophen-yl, benzofuran-yl or benzimidazolyl, or substituted indolyl.

19. A composition according to claim 15 wherein X is oxygen, Z is a covalent bond, $R_1$ is hydroxy, $R_2$ is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, benzothiophen-2-yl, benzofuran-2-yl, thiazolo[5,4-b]pyridine-2-yl, thieno[2,3-]pyridine-2-yl, imidazol[1,5-a]pyridine-2-yl, or indol-2-yl, or substituted 1,2,4-oxadiazol-3-yl, 1,2,4-oxadiazol-5-yl, isotniazol-5-yl, isothiazol-4-yl, 1,3,4-oxadiazol-5-yl, 1,2,5-thiadiazol-3-yl, oxazol-2-yl, thiazol-2-yl, or thiazol-4-yl, and $R_3$, $R_4$ and $R_5$ are hydrogen.

20. A composition according to claim 15 wherein X is oxygen, Z is a covalent bond, $R_1$ is hydroxy, $R_2$ is optionally 4,5,6 or 7 benzo-substituted benzothiazolyl, benzoxazolyl, benzimidazolyl, benzothiophenyl, benzofuranyl, or indolyl.

21. A composition according to claim 15 wherein $R_2$ is benzothiazol-2-yl substituted in the benzo by one trifluoroacetyl, or trifluoromethylthio, or one or two of fluoro, chloro, bromo, hydroxy, methyl, methoxy or trifluoromethyl, trifluoromethoxy, trifluoromethylthio, or two fluoro or two trifluoromethyl with one methoxy, or three fluoro or by 6,7-benzo.

22. A composition according to claim 15 wherein $R_3$ is hydrogen, 5-fluoro, 5-chloro, 5-bromo or 5-methyl, and $R_4$ is hydrogen, 6- or 7-substituted chloro, bromo, methyl, isopropyl, methoxy, nitro or trifluoromethyl; or $R_3$ and $R_4$ is 4,5-difluoro.

23. A composition according to claim 15 wherein $R_2$ is optionally substituted benzothiazol-2-yl or quinoxalyl, and $R_3$ and $R_4$ are each chloro.

24. A composition according to claim 15 wherein X is oxygen, Z is a covalent bond, $R_1$ is hydroxy, $R_3$, $R_4$ and $R_5$ are hydrogen, and $R_2$ is 5-bromo-2-benzothiazolyl, 5-fluoro-2-benzothiazolyl, 5-trifluoromethyl-2-benzothiazolyl, 5-chloro-2-benzothiozolyl, 4,5-difluoro-2-benzothiazolyl, 5,7-difluoro-2-benzothiazolyl, 4,7-dichloro-2-benzothiazolyl, 5,7-dichloro-2-benzothiazolyl, or 5,7-bistrifluoromethyl-2-benzothiazolyl.

25. A composition according to claim 15 wherein said compound is in the form of the sodium salt or the N-methylglucamine salt.

26. A composition according to claim 15 wherein X is oxygen, Z is a covalent bond, $R_1$ is hydroxy, $R_2$ is optionally substituted benzothiazol-2-yl, $R_3$ and $R_4$ are hydrogen, and $R_5$ is methyl.

27. A composition according to claim 15 wherein X is oxygen, Z is a covalent bond, $R_1$ is hydroxy, $R_3$, $R_4$ and $R_5$ are hydrogen, and $R_2$ is optionally 4, 5, 6 or 7 benzo-substituted 2-trifluoromethyl-benzothiazolyl, 2-trifluoromethyl-benzoxazolyl, 2-trifluoromethyl-benzimidazolyl, 2-trifluoromethyl-benzofuran, 3-trifluoromethyl-benzofuran, 2-trifluoromethyl-benzothiophen, 3-trifluoromethyl-benzothiophen, 2-trifluoromethyl-indolyl, or 3-trifluoromethyl-indolyl.

28. A composition according to claim 15 wherein X is oxygen, Z is $CH_2$, $R_1$ is hydroxy, $R_2$ is optionally substituted benzothiazol-2-yl, benzothiazol-5-yl, benzoisothiazol-3-yl, benzoxazol-2-yl, 2-quinolyl, 2-quinoxalyl, oxazolo[4,5-b]pyridine-2-yl, or thiazolo[4,5-b]pyridine-2-yl, or substituted 1,2,4- oxadiazol-3-yl, 1,2,4-oxadiazol-5-yl, isothiazol-5-yl, isothiazol-4-yl, 1,3,4-oxadiazol-5-yl, 1,2,5-thiadiazol-3-yl, oxazol-2-yl, thiazol-2-yl, or thiazol-4-yl, and $R_3$, $R_4$ and $R_5$ are hydrogen.

29. A method of inhibiting aldose reductase activity comprising administering to a diabetic host an effective amount of a compound of claim 1.

* * * * *

UNITED STATES PATENT AND TRADEMARK OFFICE
CERTIFICATE OF CORRECTION

PATENT NO. : 4,939,140
DATED      : July 3, 1990
INVENTOR(S): J. A. Lowe, III

It is certified that error appears in the above-identified patent and that said Letters Patent is hereby corrected as shown below:

On the title page under item [63], line 4 thereof, replace "July 11, 1985" by -- November 7, 1985 --.

Signed and Sealed this

Thirtieth Day of November, 1993

Attest:

BRUCE LEHMAN

Attesting Officer

Commissioner of Patents and Trademarks